(12) United States Patent
Watschke et al.

(10) Patent No.: US 7,615,059 B2
(45) Date of Patent: Nov. 10, 2009

(54) SURGICAL SUTURE PASSERS AND METHODS

(75) Inventors: Brian P. Watschke, Eden Prairie, MN (US); Robert E. Lund, St. Michael, MN (US); S. Robert Kovac, Atlanta, GA (US); John W. Westrum, Jr., Prior Lake, MN (US); Johann J. Neisz, Coon Rapids, MN (US); Timothy A. Bachman, St. Paul, MN (US); Gary A. Rocheleau, Maple Grove, MN (US); Robert S. Runman, Forest Lake, MN (US)

(73) Assignee: AMS Research Corporation, Minnetonka, MN (US)

( * ) Notice: Subject to any disclaimer, the term of this patent is extended or adjusted under 35 U.S.C. 154(b) by 1512 days.

(21) Appl. No.: 10/155,710

(22) Filed: May 24, 2002

(65) Prior Publication Data

US 2003/0023250 A1 Jan. 30, 2003

Related U.S. Application Data

(60) Provisional application No. 60/294,517, filed on May 30, 2001, provisional application No. 60/325,834, filed on Sep. 28, 2001, provisional application No. 60/355,077, filed on Feb. 7, 2002.

(51) Int. Cl.
*A61B 17/04* (2006.01)
(52) U.S. Cl. ..................................................... 606/144
(58) Field of Classification Search ................. 606/139, 606/144–148, 150, 222–225, 232, 216, 228
See application file for complete search history.

(56) References Cited

U.S. PATENT DOCUMENTS

| 1,449,087 | A | | 3/1923 | Bugbee |
| 3,090,386 | A | * | 5/1963 | Babcock ...................... 606/146 |
| 3,470,875 | A | | 10/1969 | Johnson |
| 3,763,860 | A | | 10/1973 | Clarke |
| 3,946,740 | A | | 3/1976 | Bassett |
| 4,164,225 | A | | 8/1979 | Johnson et al. |
| 4,890,615 | A | | 1/1990 | Caspari et al. |

(Continued)

FOREIGN PATENT DOCUMENTS

EP 0 674 875 A1 10/1995

(Continued)

OTHER PUBLICATIONS

Brochure, Capio™ CL Suture Capturing Device, Boston Scientific Microvasive, 4 pages (1998).

(Continued)

*Primary Examiner*—Eduardo C Robert
*Assistant Examiner*—Tara R George
(74) *Attorney, Agent, or Firm*—Jose' W. Jimenez; Kimberly K. Baxter; Gregory L. Koeller

(57) ABSTRACT

A surgical instrument for suturing soft tissue is disclosed. The surgical instrument is capable of probing tissue, and preferably provides tactile feedback concerning the condition of the tissue. The instrument can then be used to pass and retrieve a suture without the need for an additional suture retrieval tool.

4 Claims, 22 Drawing Sheets

U.S. PATENT DOCUMENTS

| | | | |
|---|---|---|---|
| 4,923,461 A | | 5/1990 | Caspari et al. |
| 4,935,027 A | | 6/1990 | Yoon |
| 4,957,498 A | | 9/1990 | Caspari et al. |
| 5,188,636 A | | 2/1993 | Fedotov |
| 5,431,666 A | | 7/1995 | Sauer et al. |
| 5,478,344 A | * | 12/1995 | Stone et al. ............... 606/144 |
| 5,478,345 A | * | 12/1995 | Stone et al. ............... 606/144 |
| 5,527,321 A | | 6/1996 | Hinchliffe |
| 5,562,686 A | | 10/1996 | Sauer et al. |
| 5,591,181 A | * | 1/1997 | Stone et al. ............... 606/144 |
| 5,630,825 A | * | 5/1997 | de la Torre et al. ......... 606/148 |
| D384,413 S | | 9/1997 | Zlock et al. |
| 5,674,229 A | | 10/1997 | Tovey et al. |
| 5,674,230 A | | 10/1997 | Tovey et al. |
| 5,690,653 A | | 11/1997 | Richardson et al. |
| 5,728,107 A | * | 3/1998 | Zlock et al. ............... 606/139 |
| 5,728,113 A | * | 3/1998 | Sherts ..................... 606/145 |
| 5,730,747 A | * | 3/1998 | Ek et al. .................. 606/148 |
| 5,741,279 A | | 4/1998 | Gordon et al. |
| 5,755,729 A | * | 5/1998 | de la Torre et al. ......... 606/148 |
| 5,766,183 A | | 6/1998 | Sauer |
| 5,797,927 A | * | 8/1998 | Yoon ....................... 606/144 |
| 5,843,099 A | | 12/1998 | Nichols et al. |
| 5,871,488 A | | 2/1999 | Tovey et al. |
| 5,908,428 A | * | 6/1999 | Scirica et al. ............. 606/139 |
| 6,048,351 A | | 4/2000 | Gordon et al. |
| 6,051,006 A | * | 4/2000 | Shluzas et al. ............. 606/148 |
| 6,056,771 A | * | 5/2000 | Proto ...................... 606/222 |
| 6,190,396 B1 | * | 2/2001 | Whitin et al. .............. 606/144 |
| 6,454,778 B2 | | 9/2002 | Kortenbach |
| 6,461,366 B1 | | 10/2002 | Sequin |
| 2004/0193217 A1 | * | 9/2004 | Lubbers et al. ............. 606/232 |
| 2006/0173491 A1 | * | 8/2006 | Meade et al. ............... 606/222 |

FOREIGN PATENT DOCUMENTS

| | | |
|---|---|---|
| WO | WO 94/17737 A1 | 8/1994 |
| WO | WO 96/39948 A1 | 12/1996 |
| WO | WO 97/47246 | 12/1997 |

OTHER PUBLICATIONS

Brochure, Capio™ CL Transvaginal Suture Capturing Device, Boston Scientific Microvasive, 4 pages (2000).

Brochure, Executive Summary: ONUX Medical, 4 pages (no. date).

Brochure, The 7 Instruments for Highly Effective Surgeons, Vallelab, 4 pages (Apr. 2002).

Brochure, Veronikis Ligature Carrier™, Marina Medical, 2 pages from website (Nov. 6, 2002).

Guner et al, Transvaginal Sacrospinous Colpopexy for Marked Uterovaginal and Vault Prolapse, Inter. J. of Gynec. & Obstetrics, 74, pp. 165-170 (2001).

Veronikis et al, Ligature Carrier Specifically Designed for Transvaginal Sacrospinous Colpopexy, Obstetrics & Gynecology, vol. 89, No. 3 pp. 478-481 (Mar. 1977).

* cited by examiner

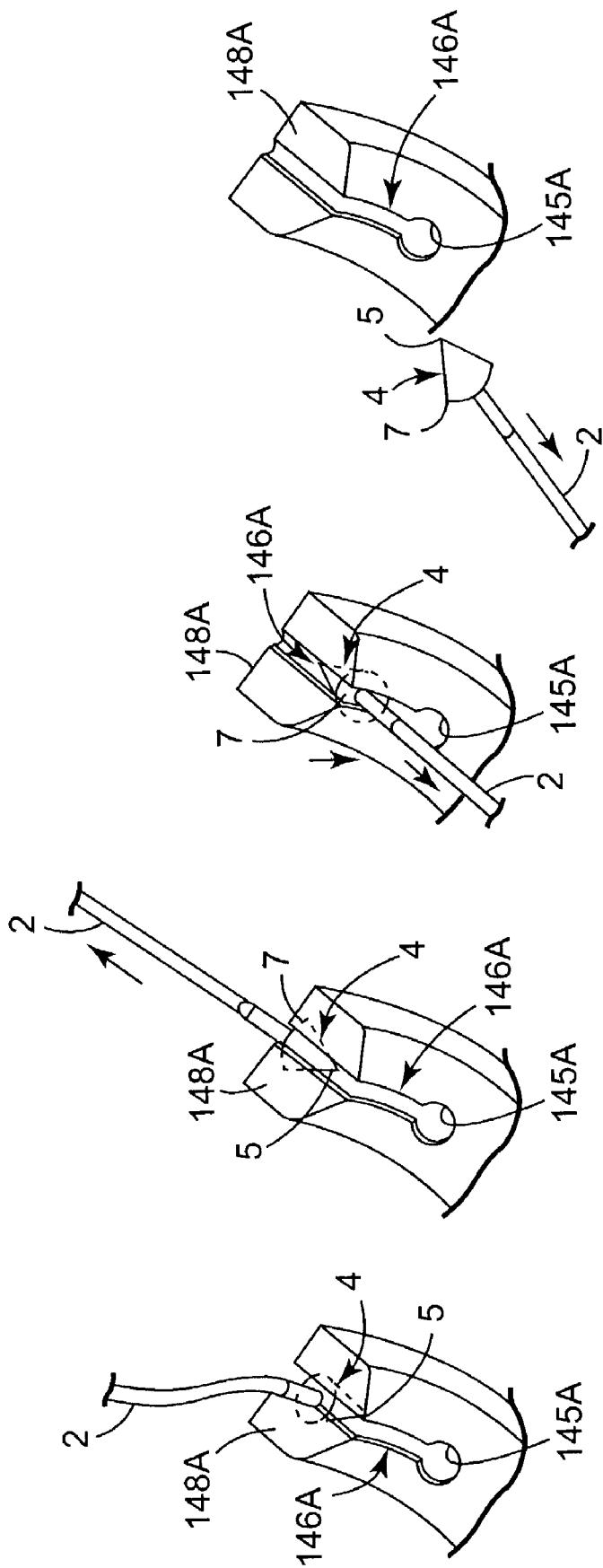

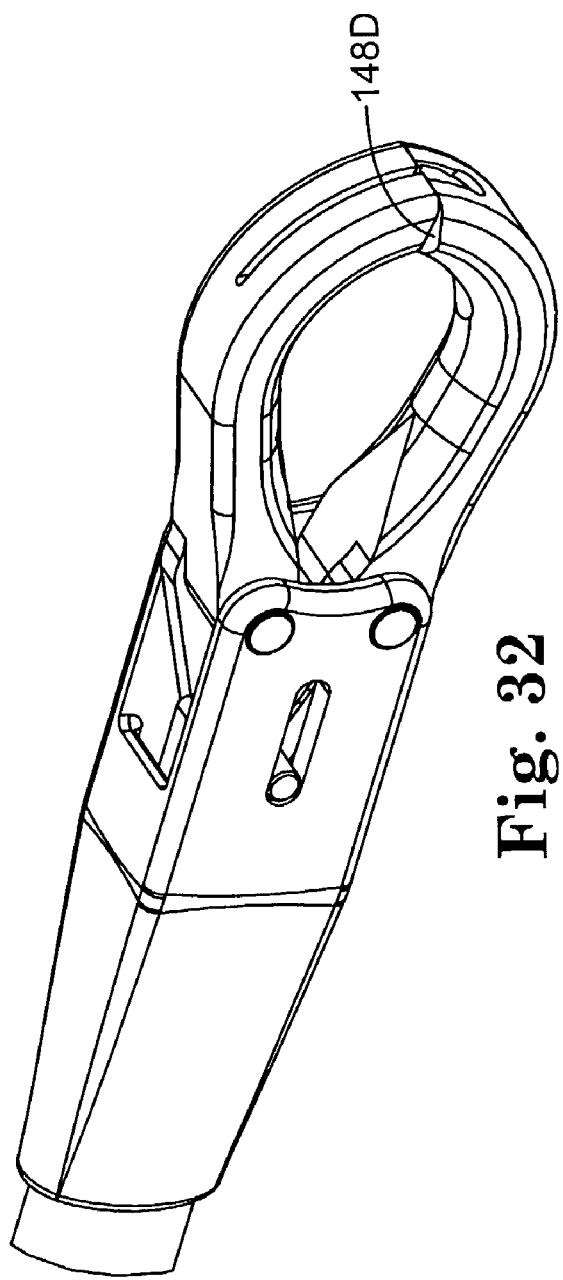
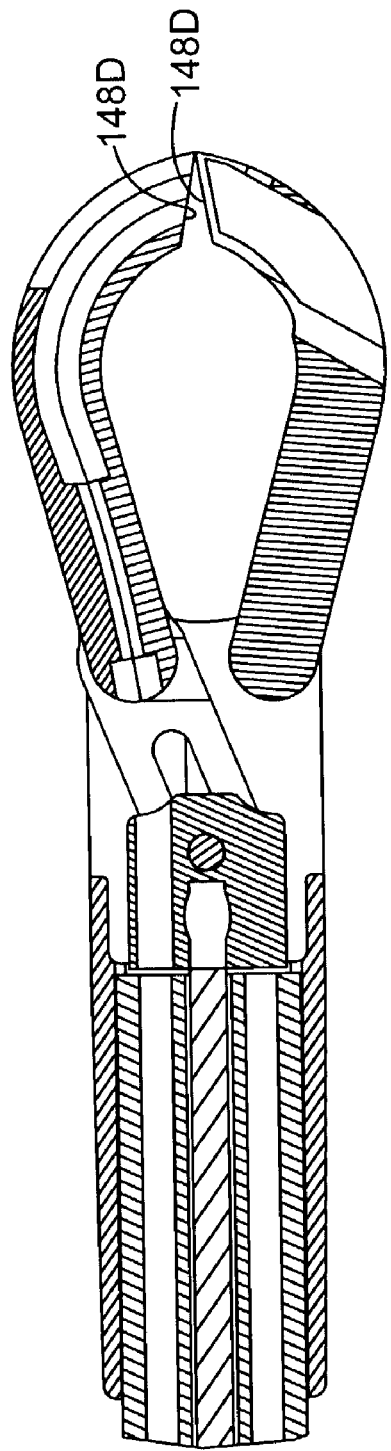

SURGICAL SUTURE PASSERS AND METHODS

CROSS REFERENCE TO RELATED APPLICATIONS

The present application claims priority to U.S. provisional patent application No. 60/294,517, filed May 30, 2001, and U.S. provisional patent application No. 60/325,834, filed Sep. 28, 2001, and U.S. provisional patent application No. 60/355,077, filed Feb. 7, 2002 (the entire contents of each of which are herein incorporated by reference in their entirety).

BACKGROUND

Surgeons often desire to test or determine the strength, character, integrity, robustness or nature of tissue during many surgical procedures. For example, a surgeon may want to gauge the strength of a region of tissue prior to subjecting that tissue to the trauma of suture passage. Surgeons often initially probe tissue with a first surgical instrument (e.g. a blunt instrument such as a Babcock clamp) and then subsequently pass a suture with a second surgical instrument (e.g. a needle). A number of problems could arise during such procedures. For example, even if suitable tissue is located, it is possible that the surgeon would be unable to find or return to the suitable tissue when the probing instrument is set aside and the second surgical instrument is retrieved. Instead, the surgeon may inadvertently mistake unsuitable tissue for the proper tissue during the hiatus between probing and suture passage.

These problems are generally more difficult when operating in an inaccessible, highly sensitive, or remote region of the patient. One such procedure involves the placement of sutures through the coccygeus muscle and/or sacrospinous ligament complex transvaginally (through a vaginal incision). Many surgical procedures require suture passage in a remote region. Examples include pelvic floor repairs utilizing sacrospinous ligament fixation.

Surgical procedures involving soft tissue repair are described in Guner et al., *Transvaginal Sacrospinous Colpopexy For Marked Uterovaginal and Vault Prolapse*, Inter. J. of Gynec. & Obstetrics, 74 (2001) Pps. 165-170; and Veronikis et al., *Ligature Carrier Specifically Designed For Transvaginal Sacrospinous Colpopexy*, J. of Obstetrics & Gynecology; Vol. 89, No. 3 Pps 478-481 (March 1997).

Examples of surgical instruments for soft tissue repair or manipulation are disclosed in U.S. Pat. Nos. 1,449,087; 3,470,875; 3,763,860; 3,946,740; 4,164,225; 4,923,461; 4,935,027; 5,527,321; 5,431,666; 5,674,230; 5,728,107; 5,730,747, 5,741,279; 5,871,488; 6,056,771 and 6,084,351. Many of these devices are unsuitable for atraumatically probing tissue. For example, some devices include a sharp trocar or needle projecting from a jaw that would damage tissue if the device were used to probe the tissue.

Some of the prior art devices do not include a suture capturing element for catching a suture after it is passed through tissue. As a result, a separate suture retrieving device (e.g. a hook) is required in addition to the prior art device to retrieve the passed suture. This is cumbersome, time consuming and may even require a second surgical personnel on some occasions.

Some of the prior art devices include jaws that pivot about one pivot point. The pivot action of the jaws pushes tissue away from the pivot point and tends to cause tissue to exude out of the open ends of the jaws. This can result in inadvertent tissue trauma, inaccurate measuring of tissue, inaccurate tissue suturing and an inability to test the structure intended to be sutured.

The Capio™ CL Transvaginal Suture Capturing Device, and the Capio™ Suture Capturing Device are available from Boston Scientific, of Natick, Mass. These devices are capable of passing a suture through tissue. However, these devices do not have jaws or other mechanisms for atraumatically probing the integrity of tissue prior to suture passage.

The ArthroSew™ Disposable Suturing Device is available from Surgical Dynamics (U.S. Surgical), of Norwalk, Conn. This device includes a sharp surgical needle that projects from its jaws. As a result, the device is not suitable for atraumatic tissue probing as the sharp surgical needle is apt to damage tissue.

The Veronikis Ligature Carrier™ is available from Marina Medical of Hollywood, Fla. The device is designed for sacrospinous ligature suspension of prolapsed vaginal vault. The device includes a needle with an eyelet and two clamp fingers. The clamp fingers do not include a mechanism for positively capturing the suture once it is passed through the tissue. As a result, an independent device (e.g. a suture retrieval hook) is required for use with this device to retrieve a suture that is passed through tissue.

BRIEF SUMMARY

The present invention is directed to surgical instruments for use in soft tissue manipulation, connection and/or repairs, particularly those encountered in urological and gynecological applications. The instruments are particularly suitable for use in soft tissue repair such as pelvic floor reconstruction procedures.

Surgical instruments according to the present invention are capable of passing a suture and dart assembly from one region (e.g. a dart transport jaw) to another region (e.g. a dart capturing jaw) where the suture and dart assembly is captured. This feature of the present invention affords suturing with a single device without the need for a separate suture retrieving device. The surgical instruments preferably allow the surgeon to probe the integrity of tissue prior to actual suture passage and provide tactile feedback concerning strength or condition of the probed tissue. The instruments are suitable for suturing in a remote region of the body.

In one aspect, the surgical instrument comprises a body portion, first and second jaws, a jaw manipulator capable of moving the jaws, a suture manipulation member for movement relative to the body portion between first and second positions in order to pass the suture and dart assembly from the first jaw to the second jaw; and an extension portion projecting distally from the body portion. The first and second jaws preferably have a major tissue gripping surface. The jaws are sized and shaped to probe tissue without substantially damaging or traumatizing the probed tissue. In a preferred embodiment, the first jaw has a channel for receiving the suture and dart assembly without any portion of the assembly projecting beyond the major tissue gripping surface of the first jaw. The second jaw has surfaces that are sized and shaped to capture the suture and dart assembly when the suture manipulation member passes the suture and dart assembly.

In another aspect, a surgical instrument preferably includes a tissue receiving region just proximal to tissue engagement surfaces. The tissue receiving region is sized and shaped for convenient operation of the instrument.

In another aspect, the present invention includes a surgical instrument with a flexible, resilient suture management member for receiving a trailing portion of a suture. The suture management member has a slot for releasably holding a trailing portion of the suture near the instrument to resist unintended entanglement of the suture on objects. Preferably, the suture management member affords advancement of the suture within the slot without substantially damaging the suture. The suture management member has a predetermined hardness.

In another aspect, the present invention includes a novel mechanism for passing the suture and dart assembly from one region to another region of the instrument. The passing mechanism preferably comprises a dart cam with a beveled distal end receivable within a substantially internal channel in a dart transport region. The beveled surface is adapted to engage a shoulder surface on the dart of the suture and dart assembly. The passing mechanism includes a pusher operatively associated with a firing member to move the dart cam from a retracted position situated within a channel of a dart transport region to a projecting position with at least a portion of the dart cam projecting beyond the dart transport region when the firing member moves from a first to a second position.

In a preferred embodiment, the dart cam has a centerline that has a distal most point that follows a path as the pusher moves the dart cam from the retracted to the projecting position. The dart is substantially right circular cone shaped with a tip and a base surface. The dart cam includes a beveled distal end that is shaped to abut the base surface of the dart to drive the tip of the dart along a path that is substantially collinear with the path of the distal point on the centerline of the dart cam during movement from the retracted to the projecting position.

In another preferred embodiment, the surgical instrument comprises a body portion, a dart transport jaw and a dart capturing jaw, a jaw manipulator capable of moving the jaws, a firing member mounted on the body portion for movement relative to the body portion between prefired and fired positions; and an extension portion projecting distally from the body portion.

In this embodiment, the dart transport and the dart capturing jaw each have a major tissue gripping surface. The jaws are operatively associated with the jaw manipulator for movement between a release position with the major tissue gripping surfaces of the jaws spaced apart to receive tissue, and a clamped position with the major tissue gripping surfaces of the jaws spaced closer together than in the release position. The jaws are sized and shaped to define a tissue receiving region that is located proximal relative to the major tissue gripping surfaces when the jaws are in the clamped position.

The dart transport jaw includes a channel capable of being loaded with at least a portion of the suture and dart assembly, and a firing assembly operatively associated with the firing member for passing the suture and dart assembly from the dart transport jaw to the dart capturing jaw when the jaws are in the clamped position.

The dart capturing jaw of the instrument includes a dart capturing member capable of associating the suture and dart assembly with the dart capturing jaw after the firing member is moved from the pre-fired to the fired position with the jaws in the clamped position.

The channel of the dart transport jaw is sized and shaped to receive the dart and suture assembly so that tissue may be approximated between the jaws without being substantially damaged by the dart and suture assembly. The channel preferably receives the dart and suture assembly without interfering with the tactile feedback provided by the device. Preferably, the dart and suture assembly is received in the channel without any portion thereof projecting beyond the major gripping surface of the dart transport jaw.

The dart capturing member is preferably adapted to releasably capture the dart to afford removal of the dart from the dart capturing jaw and subsequent reloading in the dart transport jaw so that the firing assembly can pass the suture and dart assembly from dart transport jaw to the dart capturing jaw more than once.

In another preferred embodiment, the present invention comprises a surgical instrument with dart managing surfaces that are sized and shaped to capture the suture and dart assembly when a suture manipulation member passes the suture and dart assembly. The dart managing surfaces preferably include i) engagement surfaces for holding the dart after the dart is received in the jaw and the suture is pulled in a first direction as the instrument is withdrawn from the sutured location, and ii) dart release surfaces that are sized and shaped to afford manual release of the suture and dart assembly from the jaw when the suture is pulled in a second direction that is substantially opposite said first direction.

In another aspect, the invention comprises a surgical method including the steps of: (1) providing a surgical instrument having first and second jaws movable between open and closed positions, and a firing mechanism for passing a suture and dart between the jaws, (2) loading the suture and dart assembly in the first jaw, (3) probing tissue by moving the jaws between the open and closed positions, (4) selecting tissue suitable for passage of the suture and dart assembly, (5) passing the suture and dart assembly through the selected tissue, (6) capturing the suture and dart assembly in the second jaw, and (7) threading the suture through tissue by withdrawing the device from the sutured tissue. After passage of the dart and suture assembly through tissue, the method preferably includes the step of removing the suture and dart assembly from the second jaw, and reloading the suture and dart assembly in the first jaw to afford use of the device for multiple passages of the suture and dart assembly through tissue.

Notably, methods according to the present invention are not limited to tissue suturing per se. The present invention also contemplates a surgical method comprising the steps of: 1) providing a surgical instrument having first and second jaws movable between open and closed positions, and a firing mechanism for passing a suture and dart between the jaws when the jaws are in a closed position, 2) loading the suture and dart assembly in the first jaw, 3) approximating separate first and second structures by moving the jaws between the open and closed positions, 4) passing the suture and dart assembly through the first and second structures, 5) capturing the suture and dart assembly in the second jaw, and 6) threading the suture through the structures by withdrawing the device from the sutured location. In a preferred method, the first structure comprises an implantable material (e.g. synthetic or non-synthetic, resorbable or permanent) and the second structure comprises soft body tissue, although the device could also be used to suture two structures that are foreign to the body.

Examples of particular applications include, but are not limited to uterosacral ligament fixation, closing cut vessels, vault prolapse repair, sacrospinous ligament fixation, paravaginal defect repairs, repairs of cystoceles, rectoceles, and enteroceles, prolapse repair, and deep pelvic suturing such as hypogastric arterial ligation.

BRIEF DESCRIPTION OF THE DRAWINGS

Other features and advantages of the present invention will be seen as the following description of particular embodiments progresses in conjunction with the drawings, in which.

Figure 34:
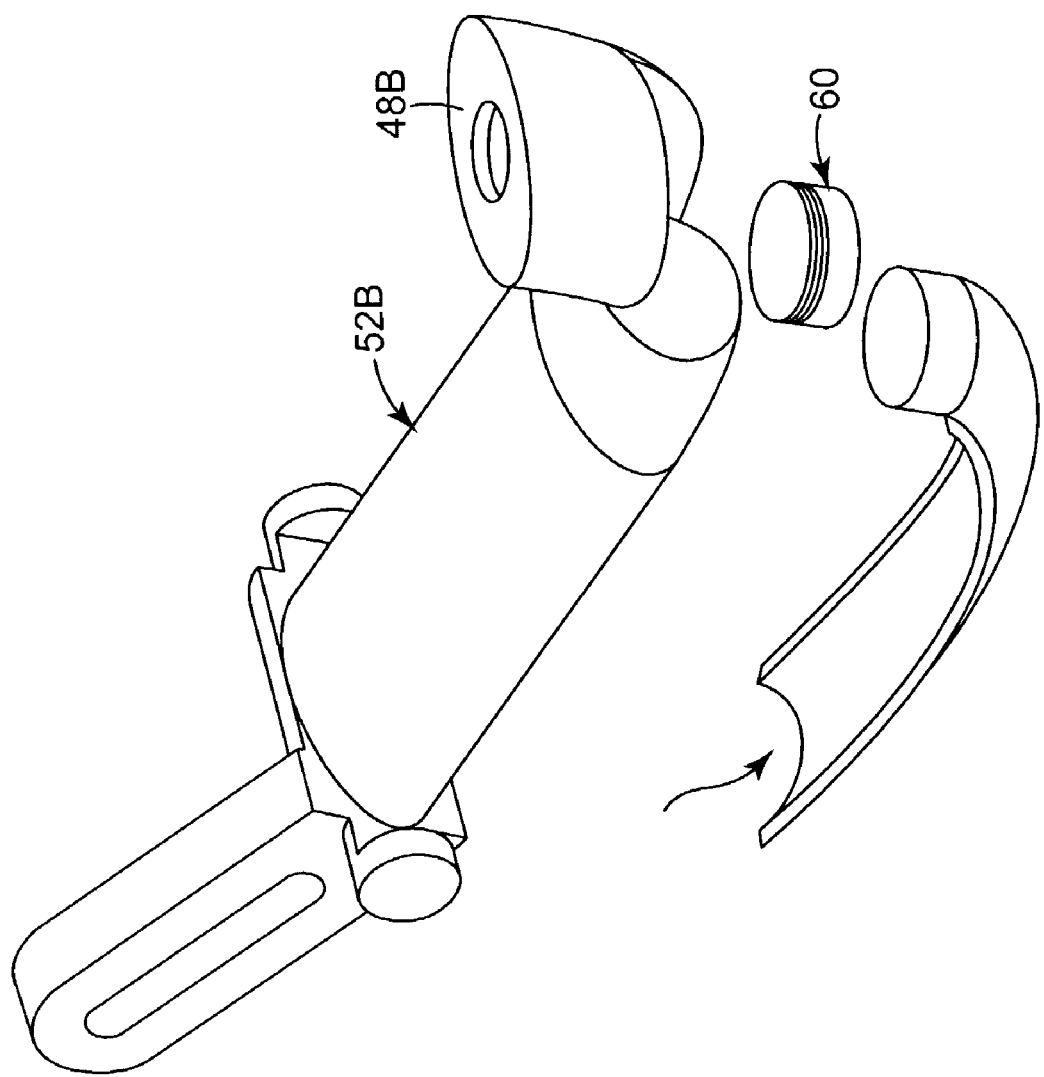
Figure 36:
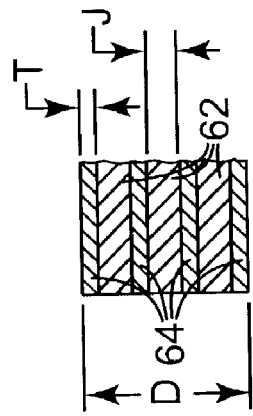
Figure 37:
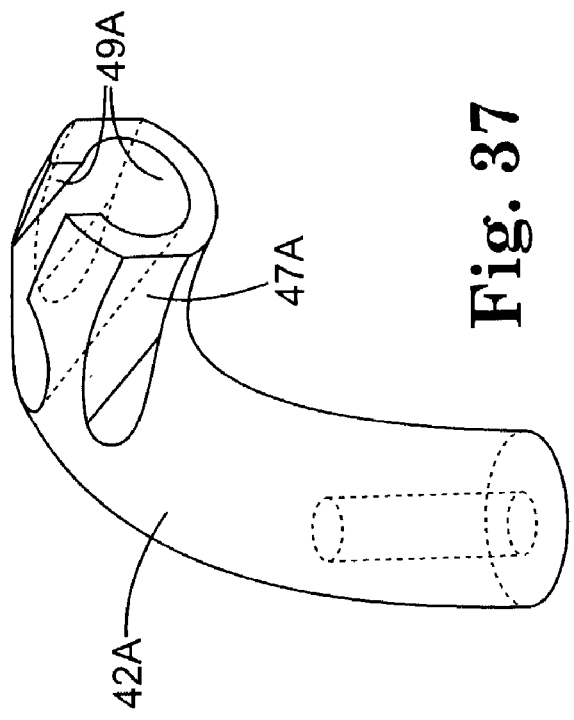
Figure 35:
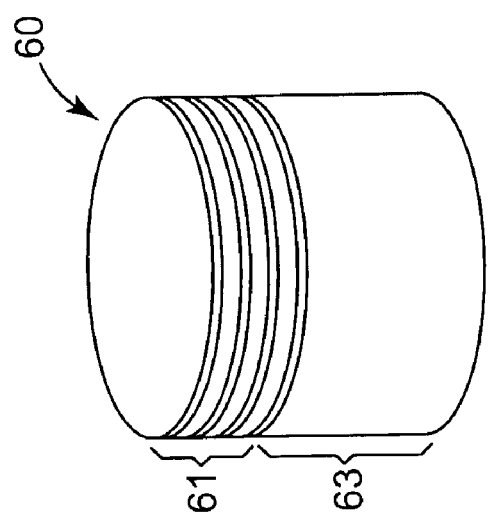

FIG.'s 28 through 31 sequentially illustrate a capture and release feature according to an aspect of the present invention, wherein:

FIG. 28 shows a dart and suture assembly just after it is captured by a dart capturing jaw;

FIG. 29 illustrates the relative positions of the elements of FIG. 28 as the device is pulled away from sutured tissue, showing the dart pivoted relative to its orientation of FIG. 28;

FIG. 30 illustrates the dart and suture assembly being pulled in a direction opposite the direction of pull in FIG. 29 in order to separate the suture and dart assembly from the jaw; and FIG. 31 illustrates the suture and dart assembly after it is removed from the jaw;

FIG. 32 is a perspective view of a distal portion of an alternate instrument according to an aspect of the present invention;

FIG. 33 is a sectional view of the instrument of FIG. 32;

FIG. 34 is a perspective view of an alternative embodiment of dart capturing jaw according to the present invention with the elements disassembled to illustrate details;

FIG. 35 is a perspective view of a dart capturing assembly according to an aspect of the present invention;

FIG. 36 is a sectional view of a component of the dart capturing assembly of FIG. 35; and FIG. 37 is a perspective view of an alternate dart cam according to the present invention.

DETAILED DESCRIPTION

The following description is meant to be illustrative only and not limiting. Other embodiments of this invention will be apparent to those of ordinary skill in the art in view of this description.

Referring to FIG.'s 1A, 2 and 3, there is shown a first embodiment of surgical device 10 according to the present invention. The device 10 is suitable for passing a suture and dart assembly through tissue, preferably in a single motion. Additionally, the device 10 can probe or test the integrity of tissue prior to actual suture passage to ensure that the tissue is desirable for suture passage. The tissue is preferably tested atraumatically so that tissue is not damaged or traumatized until the surgeon determines that the tissue is appropriate for supporting the suture. Preferably, the device 10 is capable of providing tactile feedback to the surgeon concerning the integrity of probed tissue.

The device comprises a body portion 20, a jaw portion 40 including first and second jaws 54 and 52, an extension portion 30 projecting distally from the body portion 20, jaw manipulator (e.g. levers) 22 for opening and closing jaws 52 and 54, and a suture manipulation member 24 mounted on the body portion 20 for movement relative to the body portion 20 between first and second positions in order to pass the suture and dart assembly from the first jaw 54 to the second jaw 52.

The suture manipulation member 24 is a manually actuated component for passing the suture 2 and dart 4 assembly between the jaws. Preferably, the suture manipulation member 24 comprises a pair of firing members that are positioned so that they are within easy reach of either the surgeon's thumb or index finger. Preferably, the members 24 move in unison so as one pulls back on one member they both move back. Instrument 10 may conveniently be fired with either the surgeon's index finger or thumb for advancement of the dart cam (described below).

The surgical instrument 10 affords an initial probe or grasp of tissue so that the surgeon can determine that appropriate tissue is selected. Subsequently a suture 2 is thrown, caught and retrieved from the sutured tissue at least once. These capabilities are provided in a single surgical instrument.

The first and second jaws 54 and 52 are sized and shaped to probe tissue without substantially damaging or traumatizing the probed tissue. Each jaw 52 and 54 has a major tissue gripping surface 48.

The jaw manipulating levers 22 afford a manually controlled grasping force. The jaws 52 and 54 are operatively associated with the jaw manipulating levers 22 for movement between open and closed positions. Preferably, the jaws 52 and 54 have separate pivot points 51 and 53 to provide a substantially parallel relationship between the tissue gripping surfaces 48 just adjacent the closed position.

Referring to FIG.'s 32 and 33, another embodiment of surgical instrument is shown. In this embodiment, the tissue gripping surfaces 148D are slightly canted and are not in a substantially parallel relationship in the closed position.

Returning to FIG.'s 1A, 2, 3 and 10, the surgical instrument 10 has the additional advantage of allowing a single bent device to be produced as opposed to two instruments, one with a right angle bend and one with a left. Since the levers 22 are symmetrical and the firing members 24 function together and in the same direction, flipping the instrument 10 over has no effect on operation. This also allows for a single instrument to be used with a bend in the device as opposed to a right hand bend and left handle bend, as the instrument can be simply flipped over to achieve the other bend.

The extension portion 30 preferably includes a tube 32 with a substantially oval cross sectional shape. The extension portion 30 preferably includes the bend (e.g. 15 degrees) just adjacent the jaws 52 and 54. The bend affords offset visualization of the suture passage site. Alternatively the extension portion 30 may be cylindrical with a substantially circular cross sectional shape.

The length of the device 10 is preferably sufficient to reach remote tissue within the body of a patient. For example, the length of the device 10 should be sufficient to reach the sacrospinous ligament through a vaginal incision. The length of the extension portion should be longer than two inches (to reach remote regions) and less than twenty five (25) inches. As an example, not intended to be limiting, the length of the extension portion may be about nine inches and the overall length of the device 10 may be about sixteen inches.

The mechanism for opening and closing the jaws 52 and 54 is preferably independent of the mechanism for passing the suture and dart assembly between the jaws 52 and 54. Preferably, the assembly (e.g. the firing assembly) for passing the suture and dart includes a pusher 44 that is operatively associated with first and second firing members 24. The pusher 44 is affixed to a pusher slider 31 and is preferably constructed from a rigid material such as stainless steel (e.g. ⅛ temper stainless steel wire).

The firing member 24 may be pivotally attached to the body portion 20 via pivot 25. The pusher slider 31 may have pins (e.g. projecting in a direction perpendicular to the axis of the instrument 10) that are received in slots on arms extending from the firing members 24. The pin and slot connection allows proximal pivoting of the firing member 24 to move the pusher 44 distally. Distal pivoting of the firing member 24 returns the pusher 44 proximally. The pusher slider 31 is preferably constructed from a rigid, low friction material. Suitable non-limiting examples include Nylon (e.g. 30% glass filled Nylon) and Delrin.

Referring to FIG.'s 1A, 2, 3 and 10, the mechanism for opening and closing the jaws 52 and 54 preferably comprises a pair of levers 22 and bars 23 with keys associated with a linkage 29 with keyslots for receiving keys of the bars 23. Alternatively, the levers 22 may be replaced with thumb and/or finger rings or a scissors-like handle. Levers are preferred as they do not encompass the surgeon's digits so that the surgeon can conveniently release his or her grip on the instrument 10 without disrupting the jaws 52 and 54.

The levers 22 preferably lay in the palm of the user's hand and are operated by opening and closing the user's hand. This allows for a wide variety of gripping styles to accommodate surgeon preferences and provides more freedom of movement with the tool in the hand of the operator. The levers 22 project from the body portion 20 to provide large, dispersed surface area to contribute to a preferred tactile feedback feature provided by the instrument 10.

As the levers 22 of the instrument 10 are squeezed together (note the arrow in FIG. 20), a drive rod 33 that is affixed to linkage 29 is withdrawn. The drive rod 33 associates the levers 22 with the jaws 51 and 54. Proximal movement of the drive rod 33 closes the jaws 52 and 54 on the distal end.

The linkage 29 is attached to the drive rod 33. The drive rod 33 projects through a passageway within the pusher slider 31. The linkage 29 is operatively associated with the jaws 52 and 54 to move the jaws between an open (e.g. release or tissue accept) position and a closed (e.g. clamped or tissue grasping) position. The drive rod 33 is movable relative to and within the pusher slider 31 so that the mechanism for closing and opening the jaws 52 and 54 operates independently of the mechanism for firing the suture. This helps ensure that repeated probing by the jaws will not substantially affect the firing mechanism. Optionally, wave washers may be utilized in linkage of the firing members 24 and the pusher slider 31 to help ensure independent operation.

Figure 3:
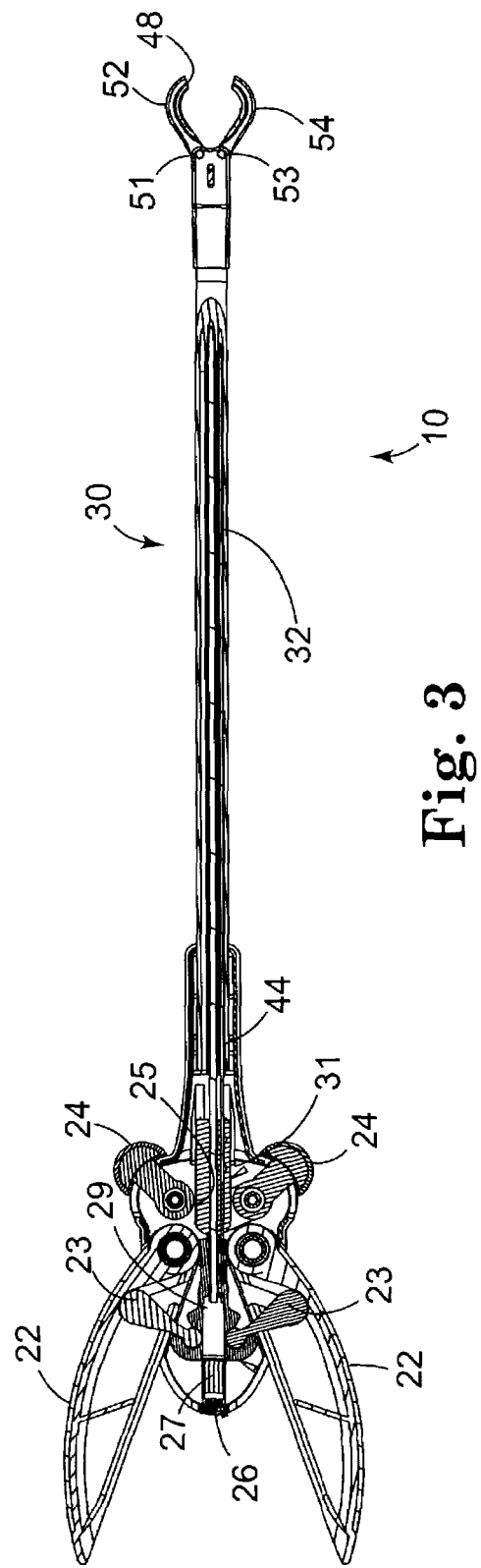
FIG. 3 is a sectional view of the surgical instrument of FIG. 2, taken approximately along lines 3-3 in FIG. 2.

A biasing means 27 such as a coil spring is preferably used to bias the jaws 52 and 54 toward the open position (FIG. 3). The levers 22 are biased by virtue of spring 27 acting on linkage 29 to resist closing of the jaws. As an example, not intended to be limiting, the spring may comprise a stainless steel coil spring with a spring constant of 12 lbs/inch. Commercial suppliers of coil springs include Century Springs (e.g. classification: Model no. 156B). This allows the jaws to return to the open position automatically when the pressure to close the jaws is removed. This simplifies the usage of the tool, as the surgeon does not have to manually open the jaws after closing them while probing and taking multiple grasps of tissue.

Preferably, the device 10 includes a suture management feature 26 described in greater detail below.

Referring to FIG.'s 1, 4, 5 and 6, there is shown another embodiment of device 100 according to the present invention. The device 100 is preferably symmetrical in that it may be used by either hand of a surgeon or in a plurality of orientations.

Figure 27:
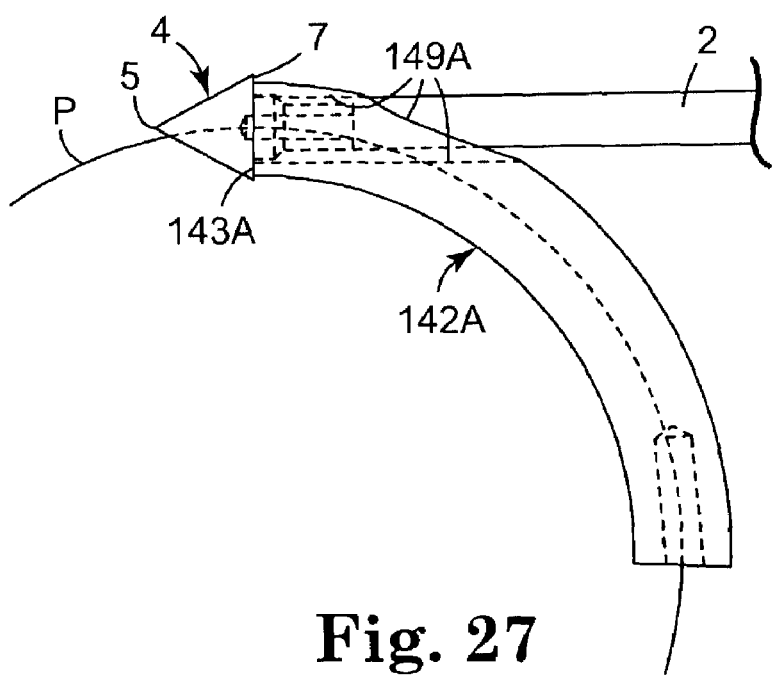
FIG. 27 is a side view of another embodiment of dart cam showing a different path for the tip of the dart caused by the dart cam.

The device 100 is particularly suitable for passing a suture 2 and dart assembly. The suture 2 and dart assembly can comprise any suitable assembly. As used herein, the term "suture and dart assembly" is used broadly to include any suture and any structure that affords passage of a suture through tissue. For example, the dart may comprise a substantially right circular cone shaped dart 4 with a sharp tip 5 and a base surface 7 (FIG. 27). The dart 4 may be constructed from stainless steel (e.g. 17-4 PH 630 SST) and include a neck portion capable of being crimped or swaged to an end of a suture. For example, the cone may have an included angle of about 41 degrees, a base diameter of about 0.075 inches. The overall length of the dart may be about 0.17 inches and the length of the cone may be about 0.1 inches.

As another example, not intended to be limiting, the dart of the assembly can include trocar-like sharp cutting surfaces that intersect at a sharp tip. A commercial example of such assembly includes a Capio Braided Polyester 0 Suture with tapercut, available from Boston Scientific Corp. of Watertown, Mass. Suitable materials for the dart include, for example, titanium and stainless steel.

The sutures may comprise any suitable sutures including monofilament and braided sutures. The sutures may be constructed from a resorbable material or a substantially permanent material such as polyester. A commercial example of an absorbable suture is the Bondek® Braided Synthetic Absorbable PGA (polyglycolic acid) Suture, available from Genzyme. In another embodiment, the dart may comprise a needle like structure. Commercial examples of such assemblies include Surgilene Monofilament Polypropylene Suture assemblies available from Davis & Geck, and the Prolene Monofilament Polypropylene Sutures available from Ethicon, Inc.

The device 100 comprises a body portion 120, a distal portion 140 with a dart transport jaw 154 and a dart capturing jaw 152, and a jaw manipulator (preferably levers 122) capable of moving the jaws 152 and 154. The instrument includes a firing member (preferably a pair of firing members 124) mounted on the body portion 120 for movement relative to the body portion 120 between prefired (FIG. 20) and fired positions (see FIG. 23).

Figure 1:
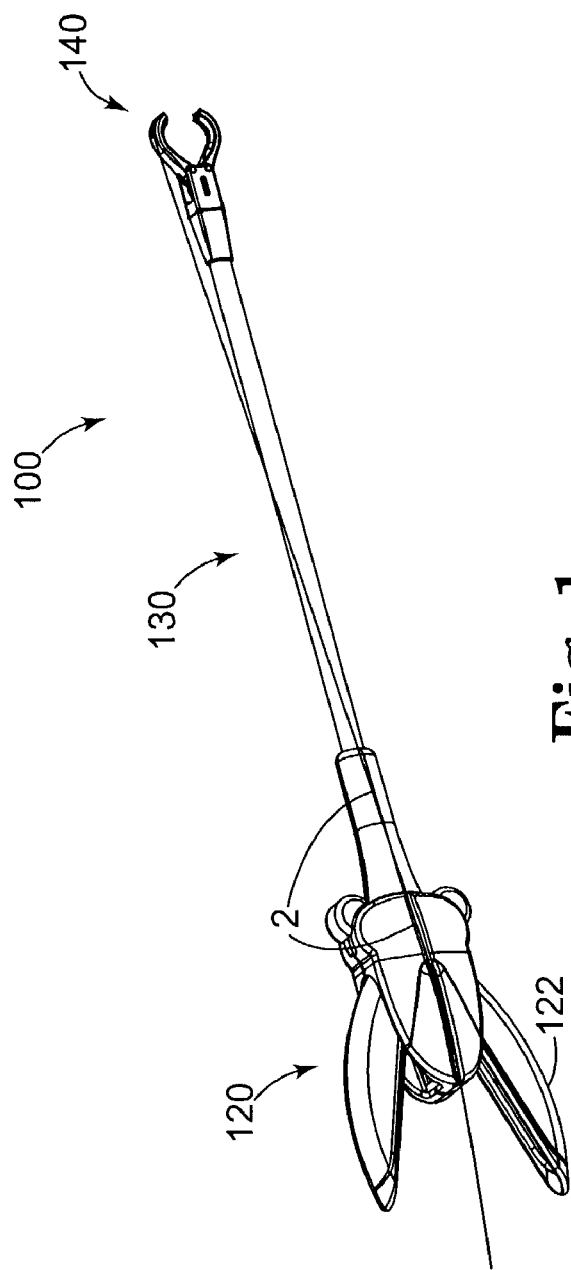
FIG. 1 is a perspective view of a surgical instrument according to an embodiment of the present invention.
Figure 1A:
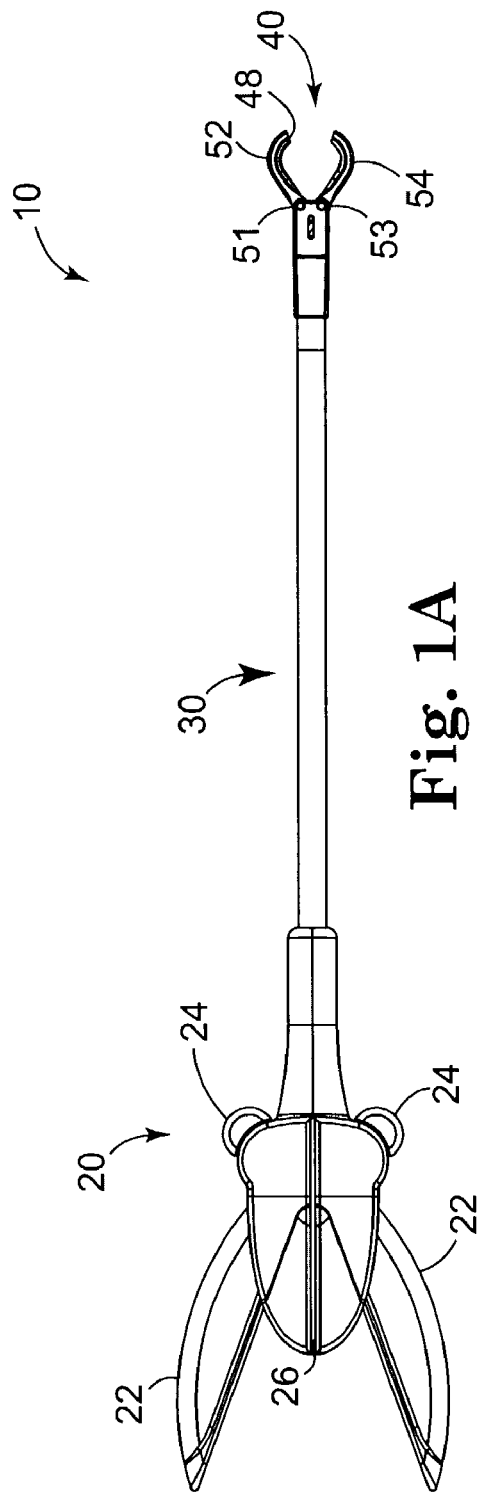
FIG. 1A is a side view of another embodiment of surgical instrument according to the present invention.
Figure 2:
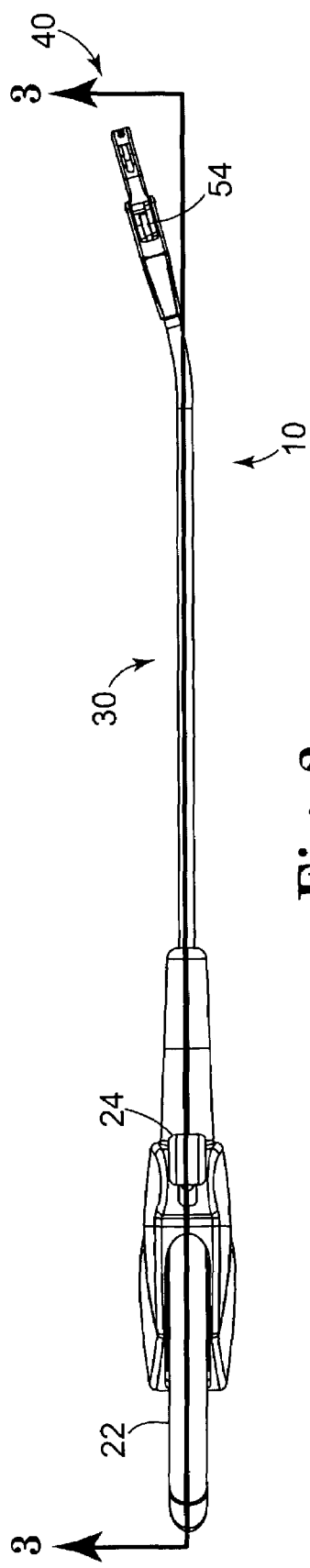
FIG. 2 is top view of the surgical instrument of FIG. 1A.

The surgical instrument 100 includes an extension portion 130 projecting distally from the body portion 120. Unlike the extension portion 30 shown in FIG. 2, the extension portion 130 does not include a bend just adjacent the jaws. The extension portion 130 may be cylindrical and the distal portion 140 constructed so that the device 100 may be threaded through a cannula-like structure and used in endoscopic or laparoscopic surgical procedures. An oval shape narrows the tool and can enhance visualization. A cylindrical shape affords convenient designs for rotating the extension to change the orientation of the jaws 152 and 154 relative to the body portion 120 in a plurality of different orientations.

The dart transport and the dart capturing jaws 152 and 154 each have a major tissue gripping surface 148. The tissue gripping surfaces 148 are preferably sized and shaped to be substantially flush in the clamped position. Preferably, each gripping surface 148 has a plurality of grasping ribs for enhancing contact between the jaws 152 and 154 and tissue. Preferably, the gripping ribs are situated substantially perpendicular to the longitudinal axis of the device 100.

The tissue gripping surfaces 148 preferably afford atraumatic probing of tissue and provide tactile feedback concerning the condition of the tissue probed. Preferably, each tissue gripping surface 148 is substantially planar (with or without grasping ribs). The outer periphery of each planar portion is between about 0.25 inches and 1.25 inches, more preferably about 0.7 inches. The cross-sectional area defined by the periphery is between about 0.005 and 0.1 square inches. If the periphery becomes too small, the force on the tissue becomes concentrated, thereby increasing the chances for undue tissue trauma. If the surface becomes too large, it may become difficult to use the device in remote, cramped regions of the body.

Figure 5:
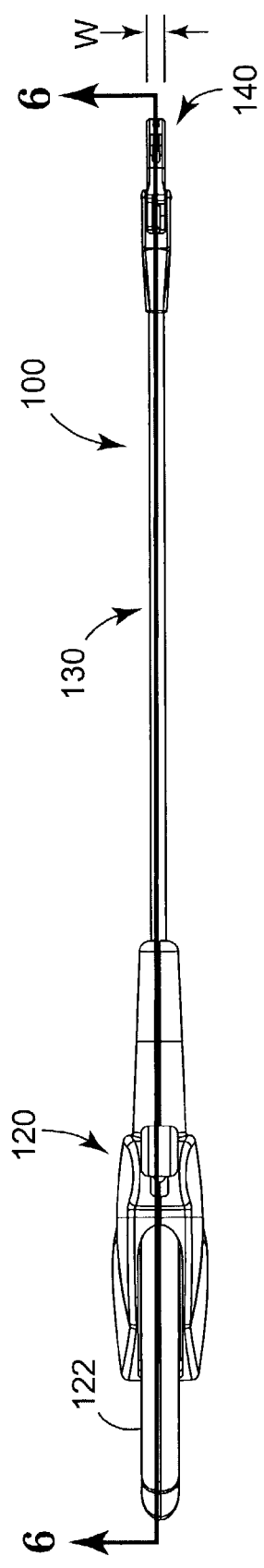
FIG. 5 is a top view of the surgical instrument of FIG. 1.
Figure 6:
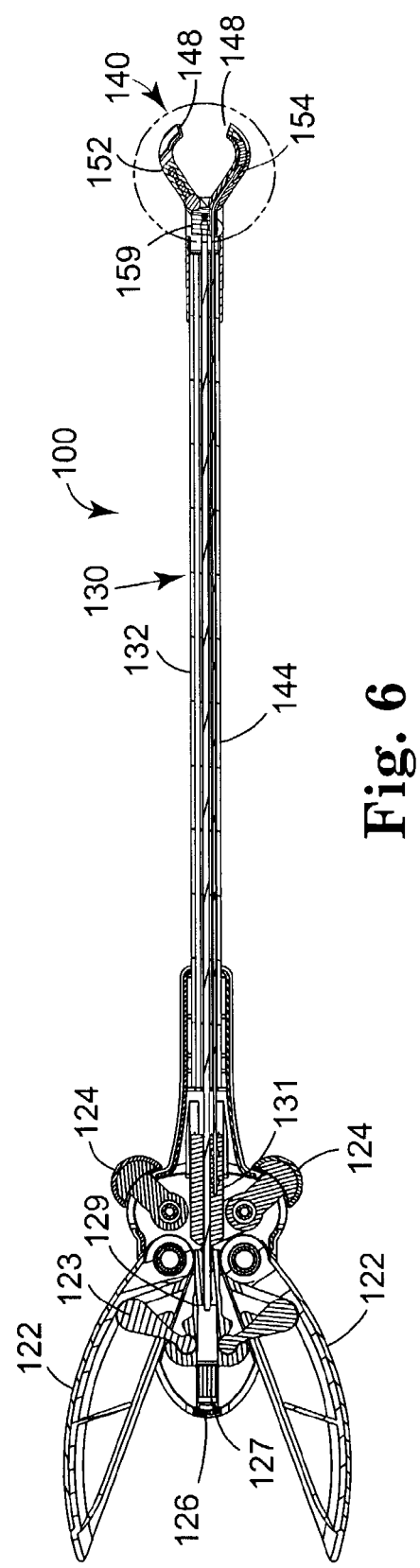
FIG. 6 is a sectional view of the instrument of FIG. 5, taken approximately along lines 6-6 in FIG. 5.

The width W (FIG. 5) of the tissue gripping surfaces is preferably small. Preferably, the width is between about 0.09 inches and about 0.4 inches, more preferably, the width is about 0.2 inches.

The jaws 152 and 154 are operatively associated with the jaw manipulator 122 for movement between a release position (FIG.'s 4 and 7A) with the major tissue gripping surfaces 148 of the jaws 152 and 154 spaced apart to receive tissue, and a clamped position (FIG.'s 20 and 7C) with the major tissue gripping surfaces of the jaws spaced closer together than in the release position. FIG. 7B shows the jaws in a position between the clamped and release positions. In the clamped position, the jaws 152 and 154 are adapted to approximate structures (e.g. tissue or implants or both) therebetween.

Referring to preferred embodiment shown in FIG.'s 6 through 7C, the mechanism for closing the jaws 152 and 154 is similar to the mechanism in the instrument 10 and comprises levers 122 and bars 123 with keys associated with linkage 129 with keyslots for receiving the keys of the bars 123. The mechanism includes a drive rod or linkage 132 (FIG. 7B) that is affixed to movable base 159. The movable base 159 includes pins that are operatively associated with slots in the jaws 152 and 154 (and slots in the distal portion 140 just proximal to points 151 and 153, see FIG. 4) to pivot the jaws about pivot points 151 and 153.

The mechanism for passing a suture preferably comprises a pusher 144 that is operatively associated with the first and second firing members 124. The pusher 144 is affixed to a pusher slider 131. The pusher slider 131 has pins that are received in slots on arms extending from the firing members 124. The pin and slot assembly affords proximal pivoting of the firing member 124 to move the pusher 144 distally. The movable base 159 includes a passageway that allows the pusher 144 to pass therethrough to afford independent operation of the tissue probing and suture firing features. The passageway can also serve to stabilize operation of the pusher 144.

Figure 7A:
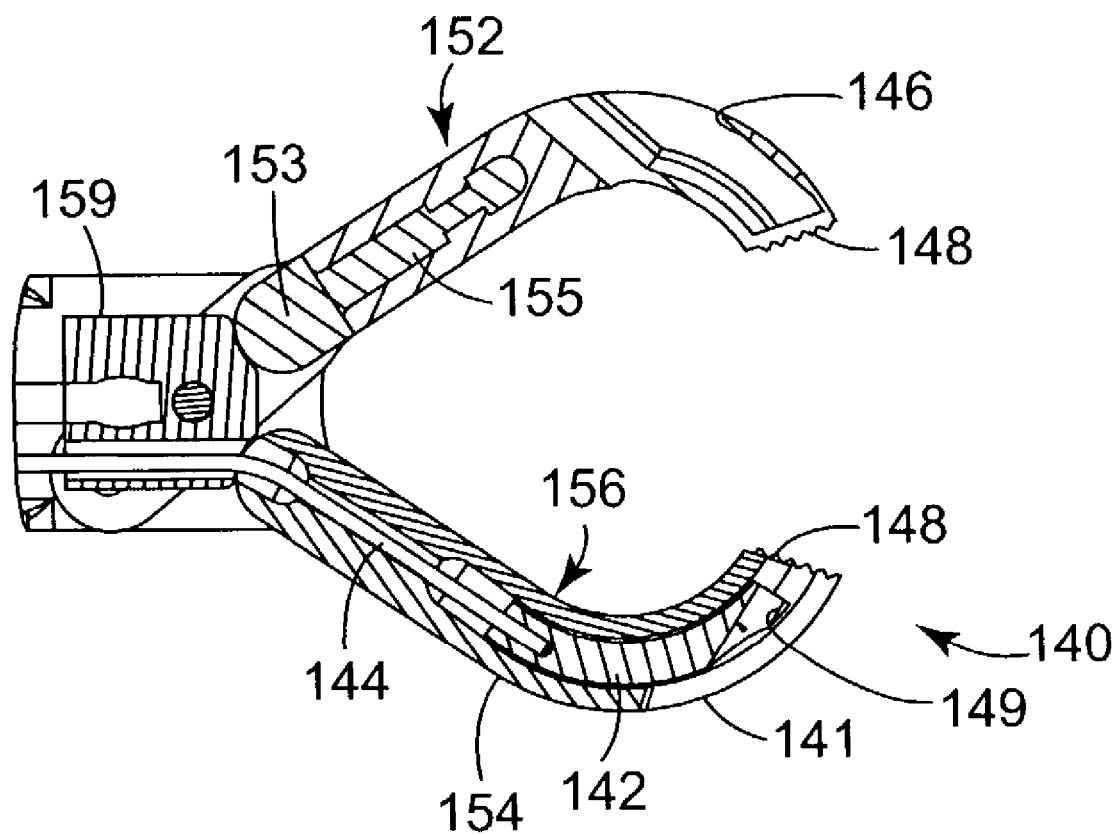
FIG. 7A is an enlarged sectional view of a portion of the device shown in FIG. 6, showing the jaws in an open position.
Figure 7B:
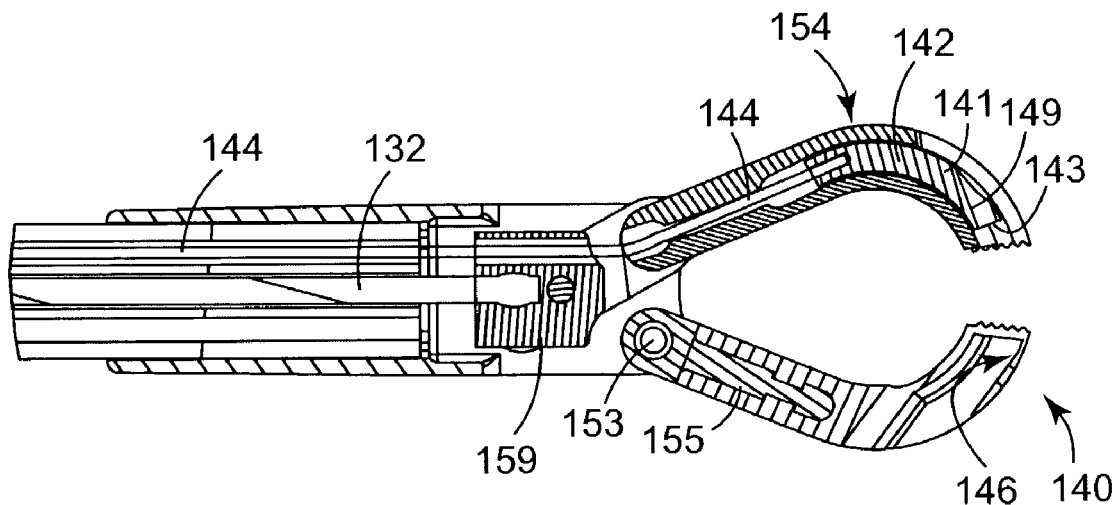
FIG. 7B is a sectional view similar to FIG. 7A (except with top and bottom jaws reversed) showing the jaws partially closed.
Figure 7C:
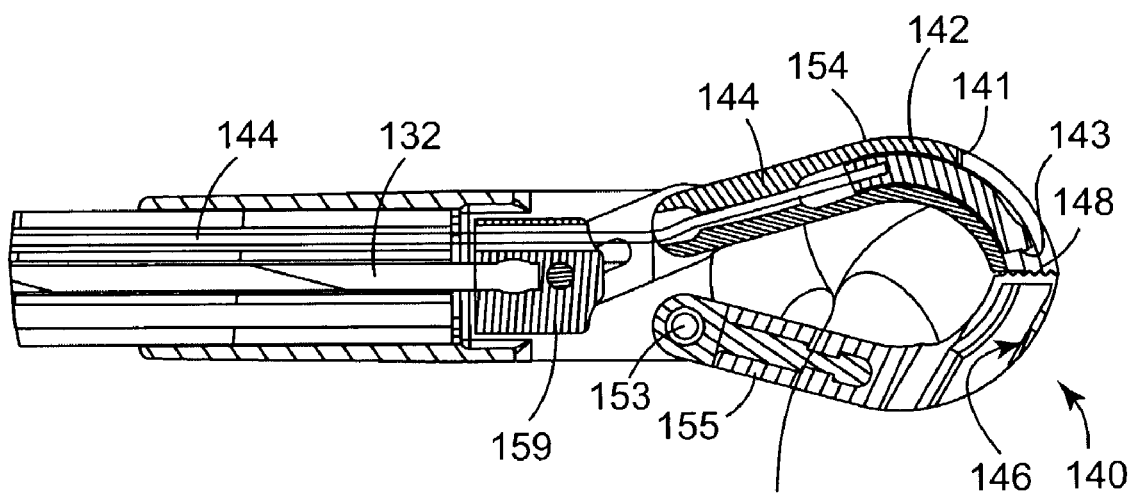
FIG. 7C is a sectional view similar to FIG. 7B showing the jaws closed.
Figure 8:
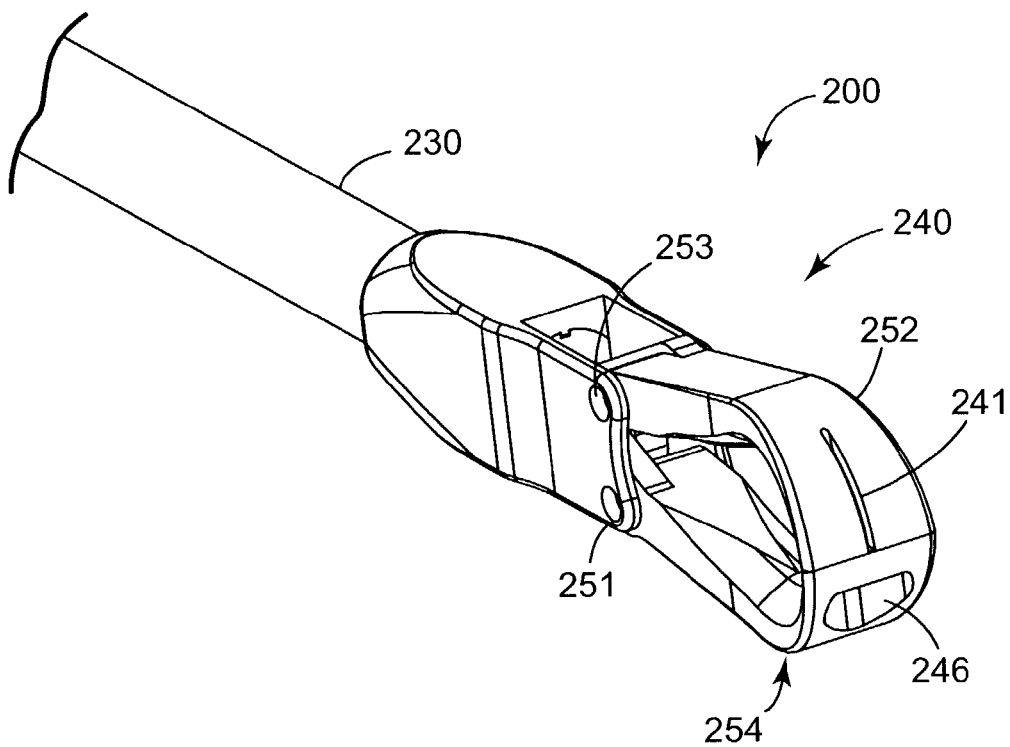
FIG. 8 is a perspective view of another embodiment of the present invention showing jaws in a closed position.
Figure 9:
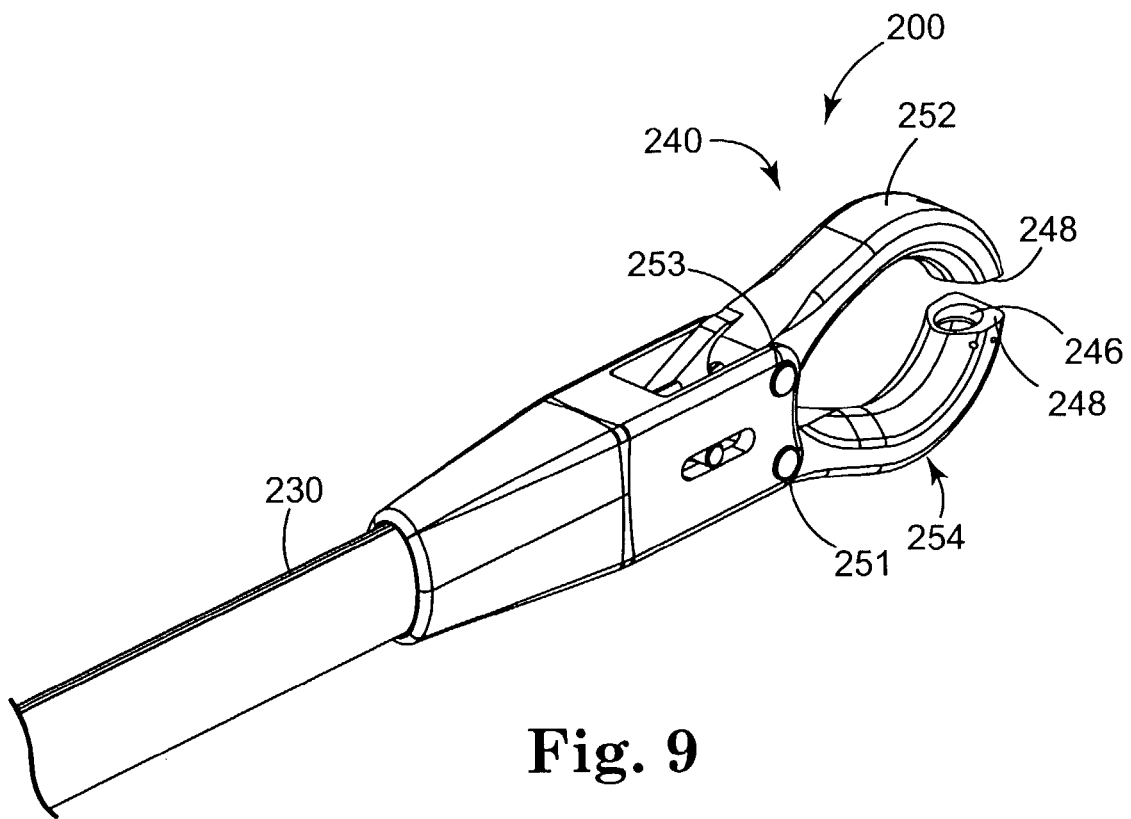
FIG. 9 is a perspective view of another embodiment, similar to the embodiment of FIG. 8, showing jaws in a partially open position.
Figure 10:
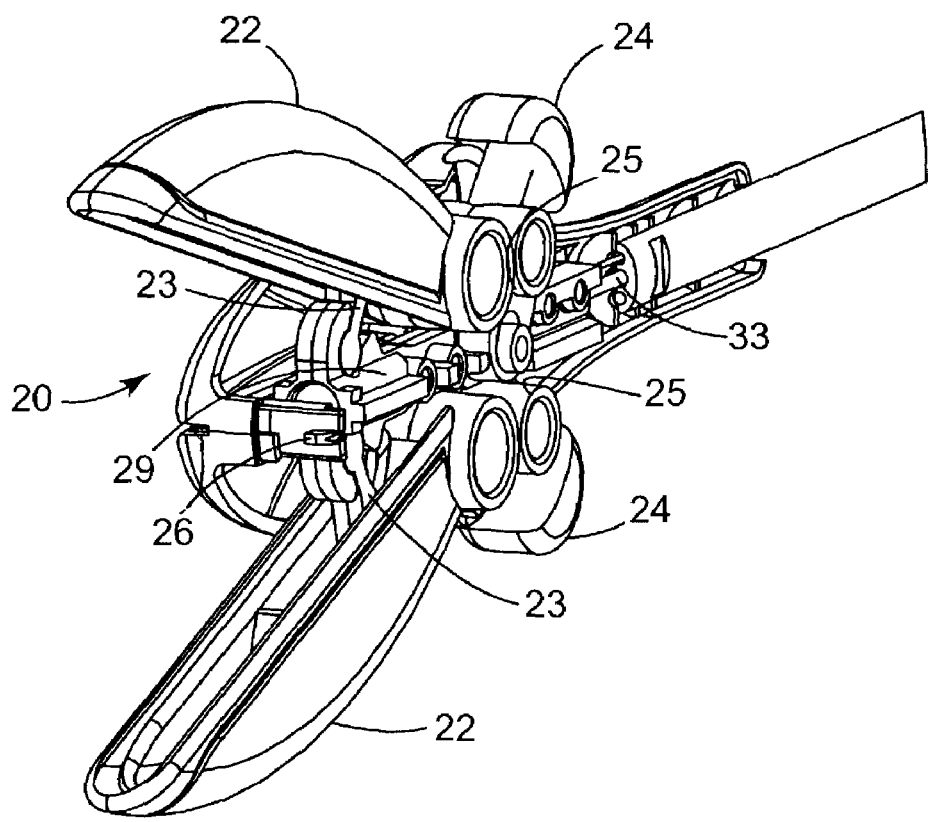
FIG. 10 is a perspective view of a proximal portion of an embodiment of the present invention with portions removed to illustrate internal details.

Referring to FIG. 7C, the jaws 152 and 154 are sized and shaped to define a tissue receiving region TRR that is located proximal relative to the major tissue gripping surfaces 148 when the jaws 152 and 154 are in the clamped position. The tissue receiving region TRR is preferably shaped to allow tissue to be atraumatically collected in this area in a substantially unclamped condition. FIG.'s 21 and 22 show the jaws 152 and 154 collecting tissue T in the tissue receiving region TRR and clamping relative to the tissue T.

The tissue receiving region TRR preferably has a cross-sectional area in the clamped position between about 0.1 square inches and 0.3 square inches, more preferably the area is about 0.19 square inches. If the area is too small, tissue will tend to exude out the distal end of the jaws, potentially resulting in unwanted tissue trauma. If the area is too large, the device may become ungainly and unsuitable for use in remote regions of the body.

The devices 10 and 100 may be manually loaded with a suture 2 and dart 4 assembly as depicted in FIG.'s 18 and 19. A slot in dart transport jaw 154 receives a portion of the suture 2 that is just adjacent dart 4. Slight tension on the suture 2 seats the dart 4 in the dart cam within jaw 154.

Referring to FIG. 7A, the dart transport jaw 154 preferably includes a channel or slot that is capable of being loaded with at least a portion of the suture 2 and dart 4 assembly. The device 100 is preferably loaded with the suture 2 and dart 4 assembly so that it can be used to probe tissue in a loaded state without interfering with the tactile feedback provided by the device 100. Preferably, when the suture 2 and dart 4 assembly are initially seated in the dart transport jaw 154, no portion of the suture 2 and dart 4 assembly projects beyond the major tissue gripping surface 148.

One approach that allows tissue to be approximated between the jaws 152 and 154 without being substantially damaged by the dart and suture assembly is to fully seat the tip of the dart 4 beneath the tissue gripping surface 148 of dart transport jaw 154. In this condition, the dart 4 and suture 2 assembly is received in the channel of jaw 154 without any portion thereof projecting beyond the major gripping surface 148 of the dart transport jaw 154. This helps avoid contact between the dart tip 5 and tissue during probing. Another alternative approach is to provide the tissue gripping surface with a shield that above the dart tip 5.

Figure 24:
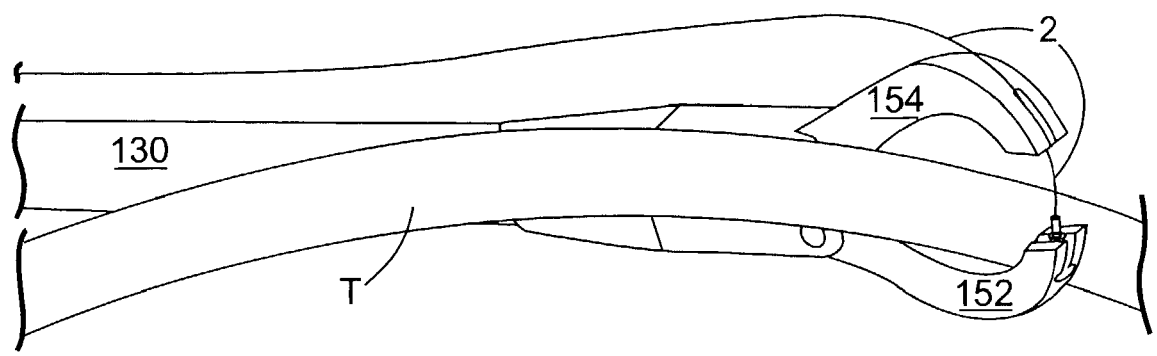
FIG. 24 is a perspective view of an embodiment of the present invention, showing the jaws in an open position after the suture and dart assembly has been passed from one jaw to the other jaw.

FIG.'s 13 through 17 illustrate a component of a preferred dart capturing jaw 152. The dart capturing jaw 152 is capable of positively capturing the dart and suture assembly after passage through tissue so that the dart and suture may be retrieved from the site of suture passage without the use of a separate suture retrieval tool. The dart capturing jaw 152 includes a dart capturing member capable of associating the suture and dart assembly with the dart capturing jaw after the suture is passed through tissue. FIG. 24 illustrates the suture and dart assembly captured in jaw 152.

Figure 23:
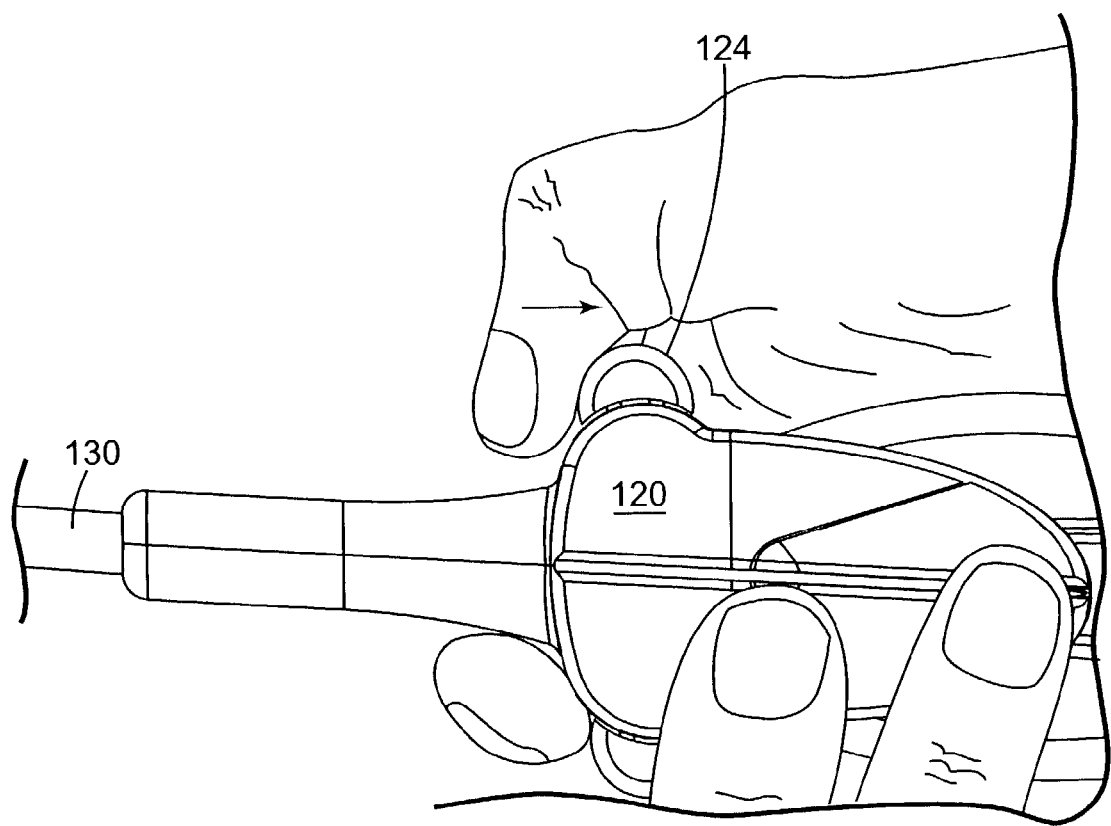
FIG. 23 is a side view showing an embodiment of the present invention with a firing member moving toward a fired position.

Like instrument 10, the device 100 includes a firing member 124 that is movable (e.g. in the direction of the arrow in FIG. 23) between a first or pre-fired position (e.g. FIG. 4) to a second or fired position (e.g. see FIG. 23). The device 100 includes a suture passing mechanism that is operatively associated with the firing member 124 for moving a suture and dart assembly from a dart transport region to a dart capturing region.

Preferably, the dart is passed between the jaws when they are in substantially a closed or clamped position. Notably, the present invention includes embodiments capable of passing the suture and dart assembly from one jaw to the other jaw while the jaws are in a substantially open or unclamped position.

Referring to FIG.'s 7A-7C and 26, a preferred suture passing mechanism is shown. The passing mechanism includes a dart cam 142 with a beveled distal end 143 receivable within a substantially internal channel 141 in the dart transport region of jaw 154. The beveled surface 143 is adapted to engage a shoulder surface 7 on the dart 4 of the suture and dart assembly. The firing/suture passing mechanism includes a pusher 144 operatively associated with the firing member 124 (e.g. via pusher slider 131) to move the dart cam 142 from a retracted position situated within the channel 141 of the dart transport region to a projecting position with at least a portion of the dart cam projecting beyond the tissue gripping surface 148 when the firing member 124 moves from the first to the second position (see FIG. 23).

Figure 26:
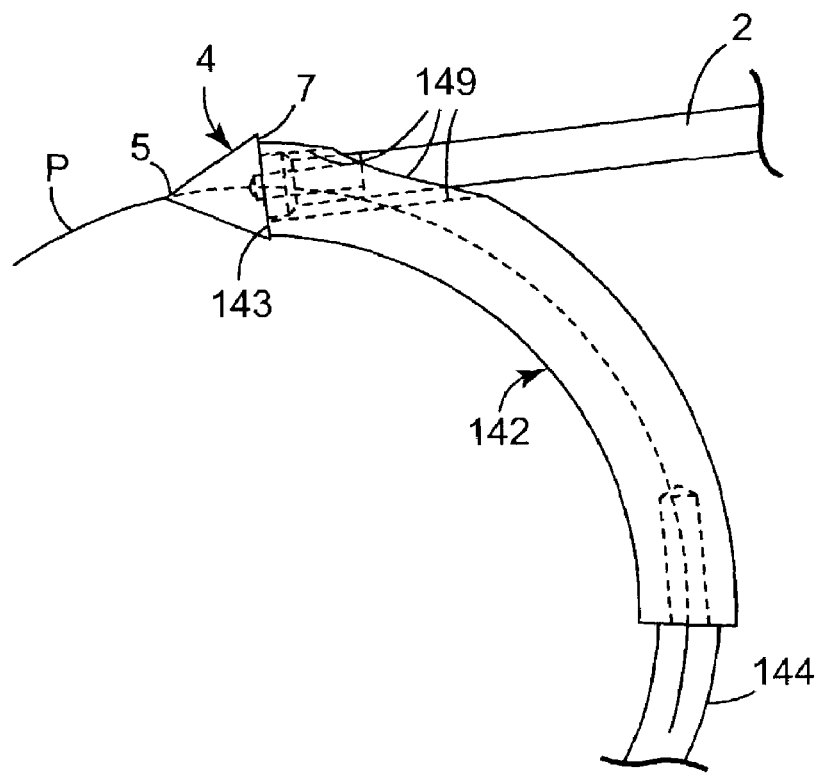
FIG. 26 is a side view of a dart cam and suture and dart assembly showing a preferred path for the tip of the dart and a distal point on the centerline of the dart cam.

Referring to FIG. 26, the dart cam 142 has a centerline with a distal most point that follows a path P as the pusher 144 moves the dart cam from the retracted to the projecting position. The dart cam 142 preferably includes a beveled distal end 143 that is shaped to abut the base surface 7 of the dart 4 to drive the tip 5 of the dart 4 along a path that is substantially colinear with the path P of the distal point on the centerline of the dart cam 142 during movement from the retracted to the projecting position. In one embodiment, the bevel is approximately five (5) degrees.

The dart cam 142 includes a slot 149 for receiving the portion of the suture 2 just adjacent dart 4 and the neck portion of the dart 4. The slot 149 helps keep the suture 2 trailing from the distal portion 140 in a preferred fashion and helps keep the suture 2 from becoming entangled on tissue adjacent the tissue to be sutured. The slot 149 also contributes to convenient loading of the device 100.

FIG. 27 discloses an alternative embodiment of dart cam 142A in accordance with another embodiment of the present invention. The dart cam 142A is not beveled, instead, it includes squared surface 143A. As a result, the tip 5 of the dart 4 shown in FIG. 27 does not follow a path that is colinear with the path P of a distal point on the centerline of the dart cam 142A. A slot 149A similar to slot 149 is included.

FIG. 37 discloses an alternative embodiment of dart cam 42A in accordance with another embodiment of the present invention. The dart cam 42A is substantially similar to dart cams 42 and 142 and includes slot 49A for receiving the portion of the suture 2 just adjacent dart 4. The dart cam 42A includes cutouts or relief portions 47A that provide additional room for a dart capturing jaw to close about the base surface 7 of a dart to more readily capture the dart.

The dart capturing jaw 152 preferably has surfaces affording release of the suture 2 and dart 4 assembly after capture so that the device 100 may be reloaded with the suture and dart assembly and used to pass the suture more than once.

FIG.'s 28 through 31 illustrate a dart capturing jaw substantially similar to dart capturing jaw 152, except that tissue gripping surface 148A is smooth (without gripping ribs). The dart capturing jaw has suture management surfaces 146A shaped to capture the suture 2 and dart 4 assembly when it is passed to the dart capturing jaw. The surfaces 146A are also adapted to release the suture and dart assembly after capture to afford reuse of the device.

Figure 13:
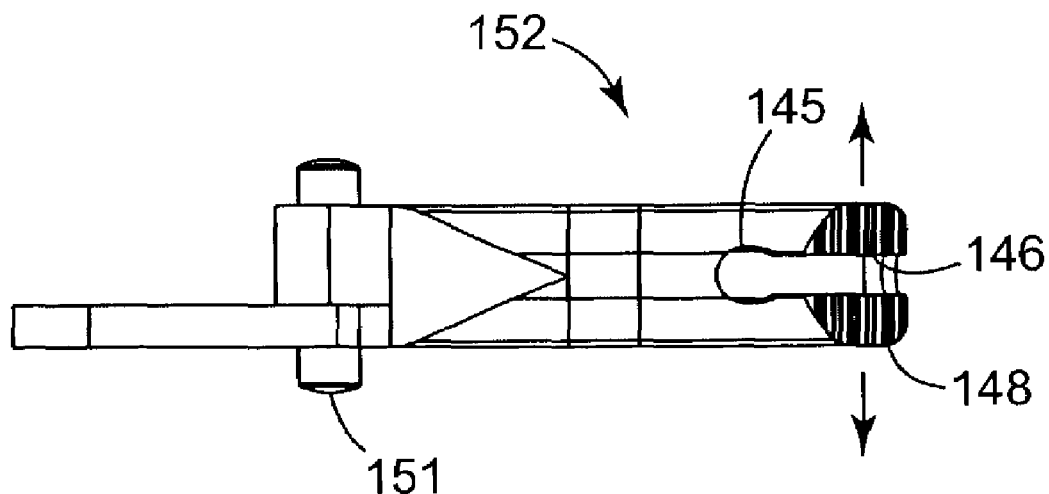
FIG. 13 is a top view of a dart capturing jaw according to an embodiment of the present invention.
Figure 14:
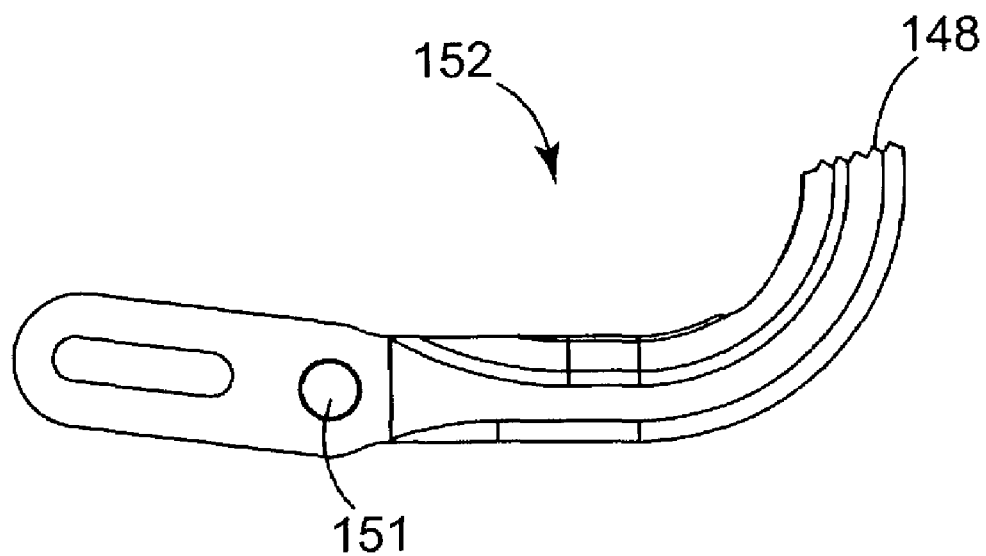
FIG. 14 is a side view of the dart capturing jaw of FIG. 13.
Figure 15:
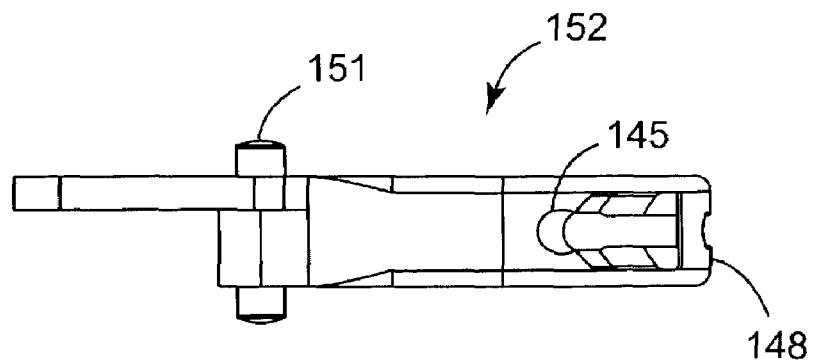
FIG. 15 is a bottom view of the dart capturing jaw of FIG. 13.
Figure 16:
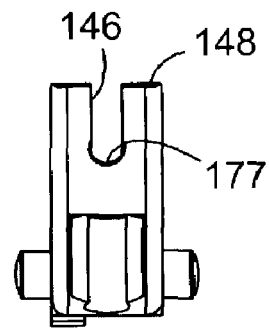
FIG. 16 is an end view of the dart capturing jaw of FIG. 13.
Figure 17:
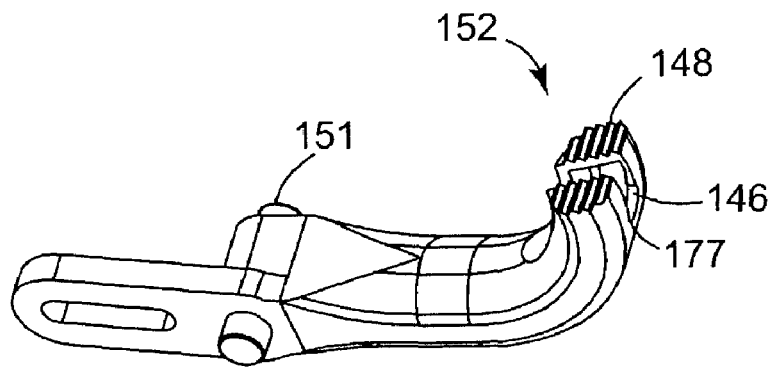
FIG. 17 is a perspective view of the dart capturing jaw of FIG. 13.

FIG. 28 illustrates the dart 4 just after it is passed to the dart receiving jaw. Preferably, the dart capturing jaw (e.g. 152) comprises first and second deflectable members with the dart managing surfaces 146 (FIG. 13) or 146A (FIG. 28) defining a slot therebetween. The first and second deflectable members are adapted to deflect (e.g. in the direction of the arrows in FIG. 13) to afford passage of the dart 4 through the slot 146A during passage of the suture and dart assembly from the dart transport jaw to the dart receiving jaw 152 (FIG. 13).

As seen in FIG.'s 7A-7C, the dart capturing jaw 152 may include a substantially rigid rod portion 155 (e.g. constructed from stainless steel or the like) and a substantially flexible material forming the first and second deflectable members (constructed from a relatively flexible material such as, but not limited to glass-filled Nylon). To assemble the dart transport jaw 154, a separate piece 156 may be used to afford access to the interior channel during assembly of the pusher 144 and cam 142.

Figure 25:
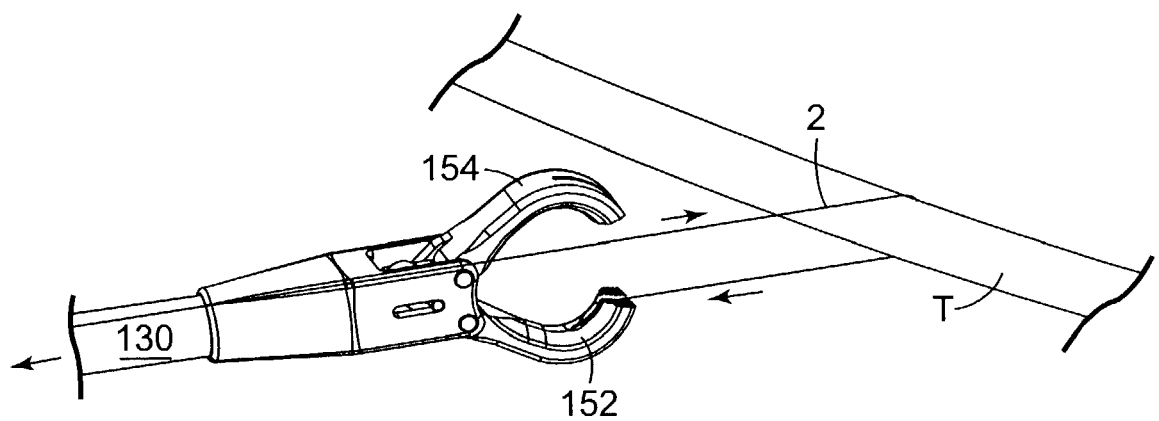
FIG. 25 is another perspective view of a device according to the present invention after the device has passed a suture through tissue, showing the device withdrawing from the location of suture passage.

The dart managing surfaces 146 include engagement surfaces 177 (see FIG.'s 16 and 17) for holding the dart 4 after the dart 4 is passed to the dart capturing jaw and the suture is pulled in a first direction as the device is withdrawn from the sutured tissue (see FIG. 25). The engagement surfaces 177 are smaller than the base 7 of the dart 4 to resist passage of the dart in a distal direction.

FIG. 25 illustrates the suture 2 and the instrument 25 when the instrument 100 is withdrawn from sutured tissue (see the arrow adjacent extension 130 in FIG. 25). The suture is threaded through tissue T in the direction of the arrows adjacent suture 2 in FIG. 25.

The dart managing surfaces 146 are preferably sized and shaped to afford pivoting of the dart 4 therein to avoid stress concentrations on the portion of the suture that attaches to the dart 4. Beveled interior surfaces can accommodate pivoting (FIG. 29) of the dart 4 and suture 2 assembly approximately ninety degrees from its orientation in FIG. 28. The arrow in FIG. 29 illustrates the tension placed on the suture 2 when the instrument 100 is withdrawn from sutured tissue (see FIG. 25).

FIG. 30 illustrates removal of the suture and dart assembly from the dart capturing jaw. The suture managing surfaces 146A preferably include dart release surfaces 145A that are sized and shaped to afford manual release of the suture and dart assembly from the dart capturing jaw when the suture is pulled in a second direction (see the direction of the arrow in FIG. 31) that is substantially opposite the first direction (see the arrow in FIG. 29). Preferably the dart release surfaces include a keyhole-like slot with a smaller slot portion (sized and shaped to afford passage of the suture 2, but not the dart 4) and the enlarged dart release surfaces 145A capable of affording passage of the dart 4. FIG. 31 illustrates the suture and dart assembly separated from the dart capturing jaw.

Referring to FIG.'s 16 and 17, the dart engagement surfaces 177 preferably include a curved surface for relieving stress in the first and second deflectable members. The curved surface is sized and shaped to block separation of the dart and the dart capturing jaw when the suture is pulled in the first direction (see the direction of the arrow of FIG. 29). In contrast, the dart release surfaces 145A are sized and shaped to afford separation of the dart and the dart capturing jaw by movement of the dart in substantially the second direction (see FIG. 31). Preferably, the dart release surfaces 145A have a diameter that is larger than the diameter of the base 7 of the dart 4.

Notably, the dart capturing jaw according to the present invention can assume a variety of forms. FIG.'s 8 and 9 illustrate instruments 200 including an extension portion 230, and a distal portion 240 with jaws 252 and 254 with pivot points 251 and 253. The tissue gripping surfaces 248 are substantially planar and flat, without any grasping ribs.

The dart capturing jaw 254 does not include a keyhole slot (e.g. 145A in FIG. 29). Instead, the portion of the dart capturing jaw 254 defining slot 246 includes a pair of internal wires (not shown) capable of capturing the dart 4.

Another embodiment of dart capturing jaws includes deflectable members defined by a slot that is situated ninety degrees relative to the slot of FIG.'s 28-31.

As the jaws open and close and grasp tissue of varying thickness, the dart cam extends out of the jaw at different lengths along the traveled arc. This leads to the dart entering the receiving jaw at a different location each time. In another embodiment of dart capturing jaw, a slot is provided so that the same grasping mechanism operates regardless of the jaw separation. Other embodiments of dart capturing jaws are described in the provisional applications from which this application claims priority.

Another version of a dart capturing jaw 52B is described in conjunction with FIG.'s 34 through 36. The dart capturing jaw 52B includes a tissue engaging surface 48B. The dart capturing jaw 52B includes a dart capturing member 60 that comprises alternating layers 61 of a relatively hard material 64 and a relatively soft material 62. The total number of layers can vary widely, but is at least two. Preferably, the relatively hard material is situated on the outside of the stack. The dart capturing member 60 may optionally include a base 63 (e.g. constructed from a 0.75 inches thick 35 durometer Shore A silicone).

Suitable hard materials 64 include, but are not limited to Mylar, polyethylene, polyvinyl chloride, polytetrafluoroethylene, polycarbonate, polyetheretherketone and polyetherketone. Suitable softer materials 62 include gel, polyethylene, rubber, foam and silicone.

Thickness T of the harder material 64 need not be the same as the thickness J of the softer material 62. The materials may be assembled with an adhesive, or preferably without an adhesive simply by pressing the materials together.

Several different samples of layered structures 61 were constructed to test pull out forces and insertion forces. Each sample was constructed using a silicone strip 0.01 inches thick (about 35-durometer Shore A) as the relatively soft material 62 (except the last sample which used polyethylene as the softer material). The harder materials were placed on the outer surface of the layered (laminate) structure. The following samples were constructed:

| Hard Material | Thickness of Hard Material | Total Thickness (e.g. see D, FIG. 36) |
| --- | --- | --- |
| 4X Mylar (Polyester) | 0.003 inches | 0.042 inches |
| 4X Polyetheretherketone | 0.003 inches | 0.043 inches |
| 4X Polyester | 0.003 inches | 0.044 inches |
| 3X Polycarbonate | 0.005 inches | 0.037 inches |
| 4X PVC | 0.004 inches | 0.047 inches |
| 4X Polyethylene | 0.005 inches | 0.049 inches |

Table 1 includes the results of the several samples used with a polypropylene monofilament suture attached to a stainless steel (e.g. 17-4 PH 630 SST) dart with conical tip with an included angle of about 56 degrees.

TABLE 1

| Laminate Material Insertion, Pull Out Force (lbs) | | | | | | |
| --- | --- | --- | --- | --- | --- | --- |
| | Insertion Force | | | | | |
| Hole Diameter (inches) of test fixture | Mylar | Polyethylene | Polyvinyl Chloride | Polycarbonate | Polyetheretherketone | Mylar Polyethylene (no silicone) |
| 0.19 | 6.75 | 5.86 | 10.25 | 9.47 | 9.58 | 8.53 |
| 0.18 | 7.12 | 6.95 | 8.90 | 10.15 | 10.03 | 10.57 |
| 0.17 | 8.17 | 7.37 | 9.47 | 10.81 | 9.64 | 10.70 |
| 0.16 | 10.79 | 7.03 | 11.04 | 10.73 | 9.44 | 9.93 |

TABLE 1-continued

Laminate Material Insertion, Pull Out Force (lbs)

| 0.15 | 8.18 | 7.33 | 11.15 | 10.76 | 9.27 | 10.29 |
|---|---|---|---|---|---|---|
| Avg | 8.20 | 6.91 | 10.16 | 10.38 | 9.59 | 10.00 |
| Std | 1.58 | 0.61 | 0.98 | 0.58 | 0.28 | 0.88 |

Pull Out Force (lbs)

| Hole Diameter (inches) of test fixture | Mylar | Polyethylene | Polyvinyl Chloride | Polycarbonate | Polyetheretherketone | Mylar Polyethylene No silicone |
|---|---|---|---|---|---|---|
| 0.19 | 7.87 | 3.02 | 2.51 | 7.83 | 3.59 | 5.86 |
| 0.18 | 6.40 | 2.99 | 1.16 | 8.51 | 4.14 | 5.31 |
| 0.17 | 8.81 | 3.06 | 3.00 | 7.23 | 3.97 | 4.30 |
| 0.16 | 7.60 | 2.96 | 2.86 | 8.08 | 3.78 | 7.15 |
| 0.15 | 6.96 | 2.99 | 3.36 | 6.63 | 3.92 | 7.04 |
| Avg | 7.53 | 3.00 | 2.58 | 7.66 | 3.88 | 5.93 |
| Std | 0.92 | 0.04 | 0.85 | 0.74 | 0.21 | 1.20 |

The tests show a variety of different materials are suitable for use in conjunction with the present invention. The Mylar/silicone combination was preferred.

Referring to FIG.'s 11 through 12, a suture management feature is shown according to another aspect of the present invention. Suture management helps keep the suture 2 from separating from the instrument 100 during use and retains the suture 2 clear from the field of view. Suture management helps keep the suture from becoming entangled with the surgeon's hand. The suture management feature resists suture tangling during deployment.

Figure 11:
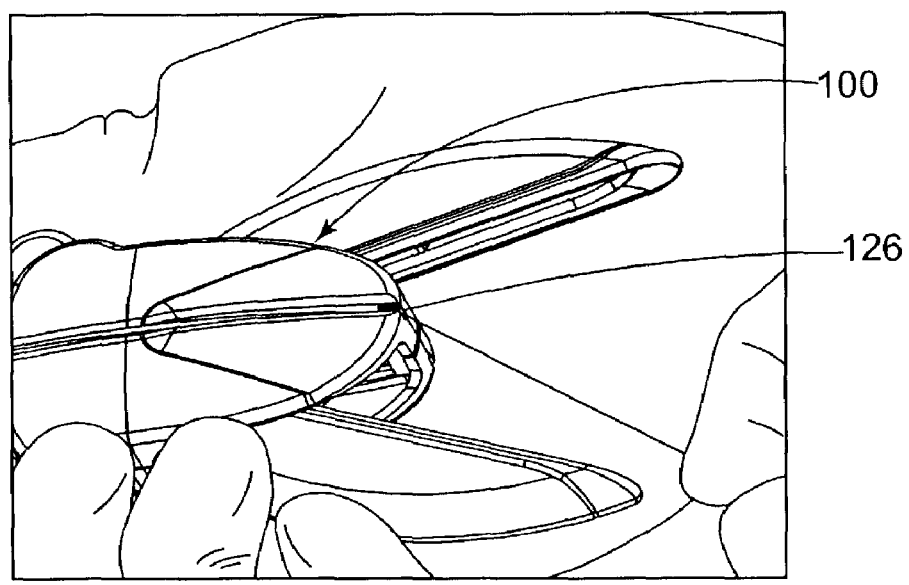
FIG. 11 is a perspective view of a proximal portion of a surgical instrument showing a suture management feature according to the present invention.
Figure 11A:
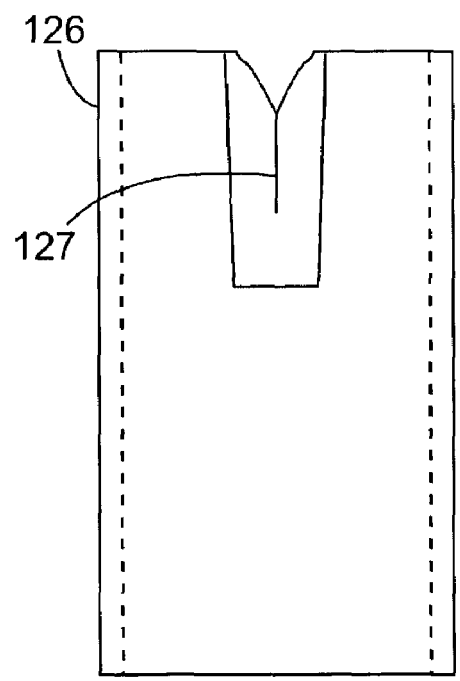
FIG. 11A is a front view of a suture management element according to an aspect of the present invention.
Figure 12:
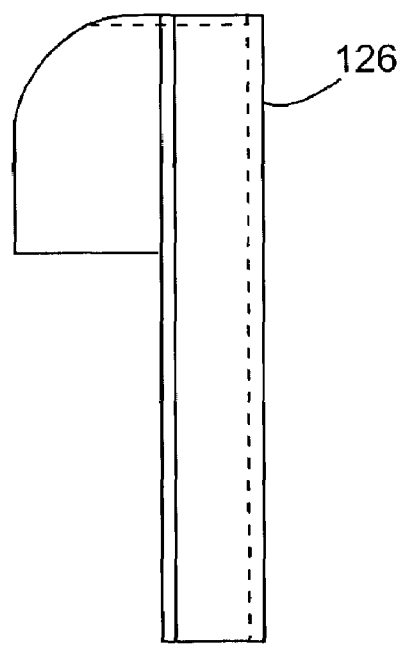
FIG. 12 is a side view of the suture management element of FIG. 11A.
Figure 11C:
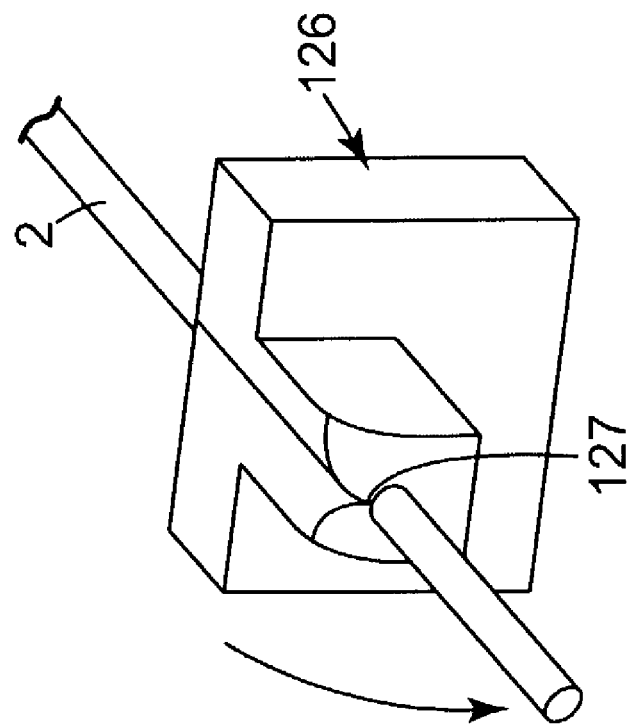
FIG. 11C is a schematic view of the suture management element of FIG. 11A with a suture inserted therein.
Figure 11B:
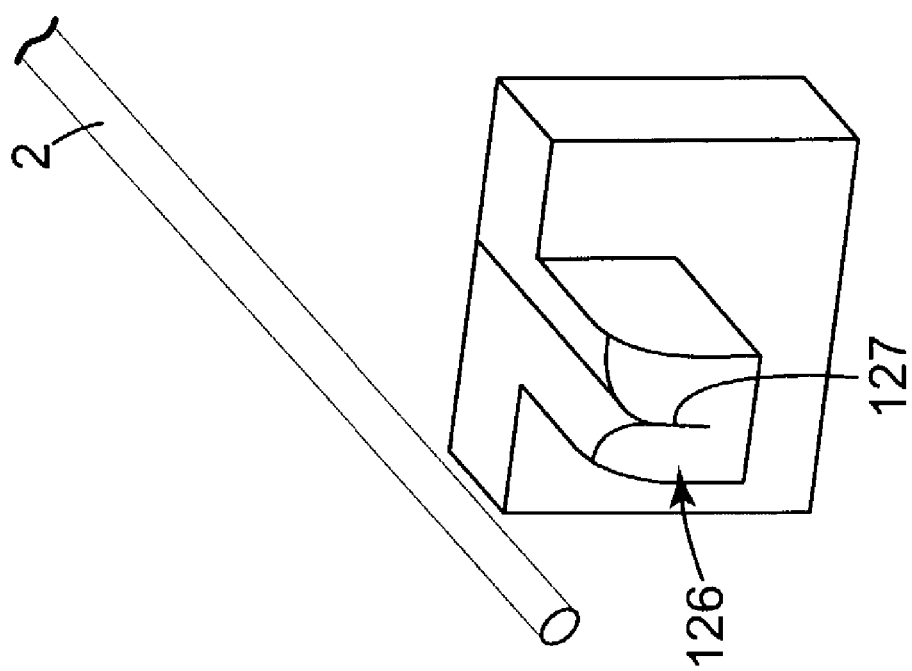
FIG. 11B is a schematic view of the suture management element of FIG. 11A and a suture spaced from the suture management element.

Preferably, the suture management feature comprises a suture management member 126 for keeping the suture 2 contained. The suture management member 126 maintains slight tension on the suture before deployment and allows it to slide during deployment and removal of the instrument from the sutured tissue (see FIG. 25). The member 126 is easy to load as the suture 2 is conveniently placed in slot 127 after the dart is seated in the jaw 154 (FIG. 11). FIG.'s 11B and 11C illustrate the suture 2 being inserted into the suture management member 126.1

Alternatively, the suture management feature may comprise the articles and assemblies described in the provisional applications from which this application claims priority.

While the suture management member 126 is particularly suitable for use with surgical devices 10 and 100, the present invention contemplates the use of the suture management member 126 with any surgical device that trails a suture from a distal portion. For example, the suture management member 126 may be used in conjunction with bone anchor insertion devices, such as the devices disclosed in U.S. patent application No. 10/133,271, filed Apr. 26, 2002 (the entire contents incorporated herein by reference). Alternatively, suturing devices such as the Capio Suture Capturing Device, the Capio CL Transvaginal Suture Capturing Device, and the ArthroSew Disposable Suturing Device, may be modified to incorporate a suture management feature according to the present invention.

The preferred suture management member 126 has a slot 127 for releasably holding a trailing portion of the suture 2 near the device (e.g. 10 or 100) to resist unintended entanglement of the suture on objects. The suture management member 126 preferably retains tension on the suture 2 and dart 4 assembly during passage of the suture and dart assembly from the dart transport jaw 154 to the dart capturing jaw 152 without substantially damaging or altering the suture. The suture management member 126 also preferably retains tension on the assembly when the device 100 is retracted from the sutured tissue (FIG. 25).

The suture management member 126 preferably affords advancement of the suture within the slot 127 without substantially damaging the suture when the instrument 100 is retracted from the suture site (FIG. 25). As shown in FIG.'s 4 and 6, the suture management member is preferably placed on a proximal portion of the body portion 120. The suture management member may be located in another position, such as on the firing member or a mid point of the body portion 120.

Figure 4:
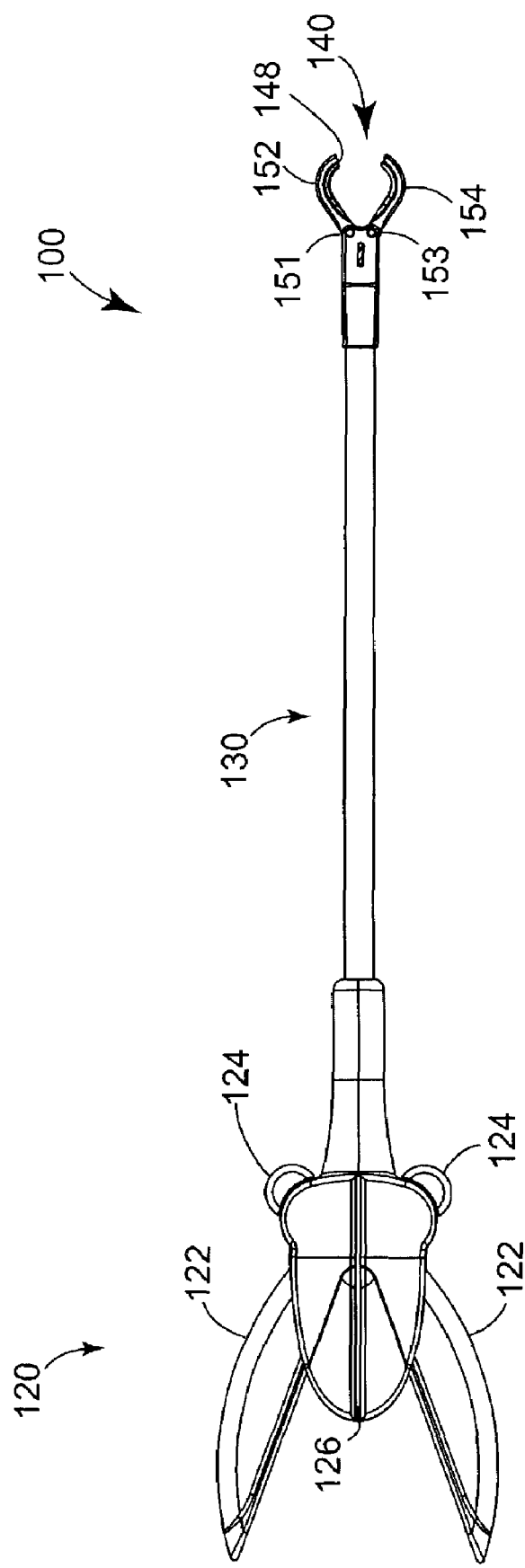
FIG. 4 is a side view of the surgical instrument of FIG. 1.

As shown in FIG. 4, the body portion 120 may include a channel, groove or slot to help hold the suture loosely in place. The slot creates a track for the suture 2 to lie in. The slot in the body portion 120 allows the suture to lie flush with the instrument 100 and avoid getting caught in the surgeon's hand during use.

The suture management element 126 is preferably located on the proximal portion of the body portion 120, on both the right and left sides of the device. The slit or slot 127 is preferably constructed in a soft material such as silicone, C-flex, foam, or other elastomeric material that would provide some gripping force due to friction on the suture. This force would be minimal though as to allow the suture to slide during deployment. The suture management member 126 preferably includes silicone with a hardness between about 20 durometer Shore A and about 80 durometer Shore A, preferably about 60 durometer Shore A. For example, the suture management member 126 may comprise 4860 Medical Silicone Elastomer, generally available from NuSil of California.

Surgical instruments according to the present invention may include various features including adjustable jaws, reloadable jaws (e.g. with a cartridge), removable jaws, modular constructions, articulating distal portions and lockout features. For example, a lockout may be provided to blocks the firing mechanism from passing a dart unless the jaws are in a clamped position. Another lockout may be provided that blocks the jaws from closing (and/or the instrument from firing) if a dart and suture assembly is not properly loaded in the dart transport jaw. Another lockout may be provided that blocks firing of the device if the jaws are deflected inappropriately. Additional surgical instruments and methods according to the present invention are described in U.S. provisional patent application No. 60/294,517, filed May 30, 2001, and U.S. provisional patent application No. 60/325,834, filed Sep. 28, 2001, and U.S. provisional patent application No. 60/355,077, filed Feb. 7, 2002. The entire contents of each of those applications is herein incorporated by reference in their entirety.

The above-described surgical instruments may be disposable or reusable. Optionally, portions of the surgical instrument may be reusable (sterilizable) and other components may be disposable.

The surgical instruments, components thereof and sutures may be provided in a kit. The kit may include components for general surgical applications or it may be customized for a particular type of surgical procedure. Other accessories may also optionally be included in a kit according to the present invention. For example, a surgical drape specifically designed for urological procedures may be included in a kit of the present invention. Such a drape is disclosed in U.S. patent application No. 09/749,254, filed Dec. 27, 2000 (the entire contents incorporated herein by reference).

The individual elements of the kits of the present invention may be packaged together, separately or in subassemblies depending on a variety of factors such as shelf life and sterilization requirements. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), or plasma procedures.

SURGICAL METHODS

In another aspect, the present invention comprises a surgical method, e.g. for 25 soft tissue repair. The soft tissue repairs associated with the present invention include pelvic floor reconstruction procedures. Examples of particular applications include, but are not limited to uterosacral ligament fixation, closing cut vessels, vault prolapse repair, sacrospinous ligament fixation, paravaginal defect repairs, repairs of cystoceles, rectoceles, and enteroceles, prolapse repair, and deep pelvic suturing such as hypogastric arterial ligation.

In general, a method comprises the steps of: (1) providing a device (e.g. 10 or 100) having first and second jaws movable between open and closed positions, and a firing mechanism for passing a suture and dart between the jaws, (2) loading the suture and dart assembly in the first jaw, (3) probing tissue by moving the jaws between the open and closed positions, (4) selecting tissue suitable for passage of the suture and dart assembly, (5) passing the suture and dart assembly through the selected tissue, (6) capturing the suture and dart assembly in the second jaw, and (7) threading the suture through tissue by withdrawing the device from the sutured tissue. After passage of the dart and suture assembly through tissue, the method preferably includes the step of removing the suture and dart assembly from the second jaw, and reloading the suture and dart assembly in the first jaw to afford use of the device for multiple passages of the suture and dart assembly through tissue.

Notably, the present invention is not limited to tissue suturing per se and contemplates a surgical method comprising the steps of: 1) providing a device having first and second jaws movable between open and closed positions, and a firing mechanism for passing a suture and dart between the jaws when the jaws are in a closed position, 2) loading the suture and dart assembly in the first jaw, 3) approximating (preferably atraumatically) separate first and second structures by moving the jaws between the open and closed positions, 4) passing the suture and dart assembly through the first and second structures, 5) capturing the suture and dart assembly in the second jaw, and 6) threading the suture through the structures by withdrawing the device from the sutured location. In a preferred method, the first structure comprises an implantable material and the second structure comprises soft body tissue, although the device could also be used to suture two structures that are foreign to the body.

The implantable material may comprise synthetic or non-synthetic materials or hybrids or combinations thereof. The implantable material can comprise a material suitable for correcting pelvic floor disorders such as a cystocele or a rectocele or a prolapse or a paravaginal defect. The implantable material may optionally comprise a sling.

Suitable non-synthetic materials include allografts, homografts, heterografts, autologous tissues, cadaveric fascia and fascia lata.

Suitably synthetic materials include polymerics, and plastics and any combination of such materials. Commercial examples of such materials include Mersile™, Teflon™, Gore-Tex™, Silastic™, Marlex™, Prolene™, and Vaskutek™. Other examples of suitable materials include those disclosed in U.S. patent application Ser. No. 09/939,098 filed Aug. 24, 2001, U.S. patent application No. 09/917,443 filed Jul. 27, 2001 and U.S. patent application No. 09/917,562 filed Jul. 27, 2001 (the entire contents of each of which are herein incorporated by reference). Specific examples of synthetic sling materials include absorbable and non-absorbable materials such as polypropylene, polyethylene, nylon, PLLA and PGA.

An example, not intended to be limiting, is a general suturing application during open or endoscopic surgery to assist in the placement of suture materials in tissues at the operative site, under direct visualization.

Figure 18:
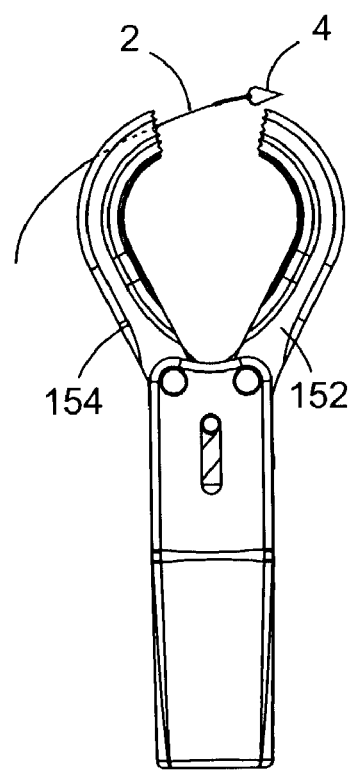
FIG. 18 is a side view showing a dart and suture assembly being loaded into a jaw according to one embodiment of the present invention.
Figure 19:
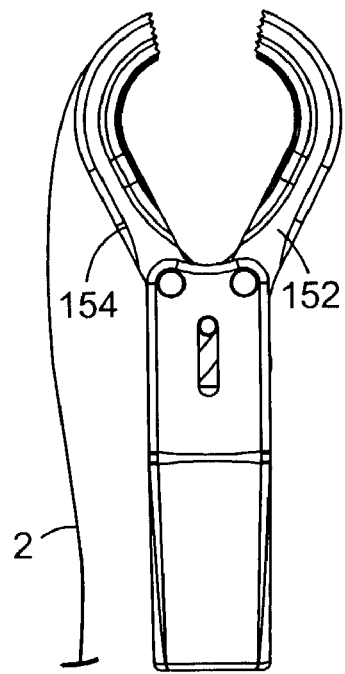
FIG. 19 is a side view of the embodiment of FIG. 18 after the suture and dart assembly is loaded within the jaw.

Initially, suture 2 is placed in the slot of the dart transport jaw (FIG. 18). One then gently pulls back on the suture 2 to draw the dart back into the dart transport jaw (FIG. 19). The device 100 may be inspected to ensure that the dart 4 is seated in the dart cam 142 and withdrawn completely into the jaw 154 so the dart 4 does not protrude out of the jaw 154. The suture 2 is gently pulled toward levers 22, keeping the suture 2 taught. The suture 2 is then loaded into the suture management system 126 (FIG. 11) by placing the suture 2 into the crevice located on the proximal portion of the body portion 120, and pulling the suture down, locking it into place (compare FIG.'s 11B and 11C).

Figure 20:
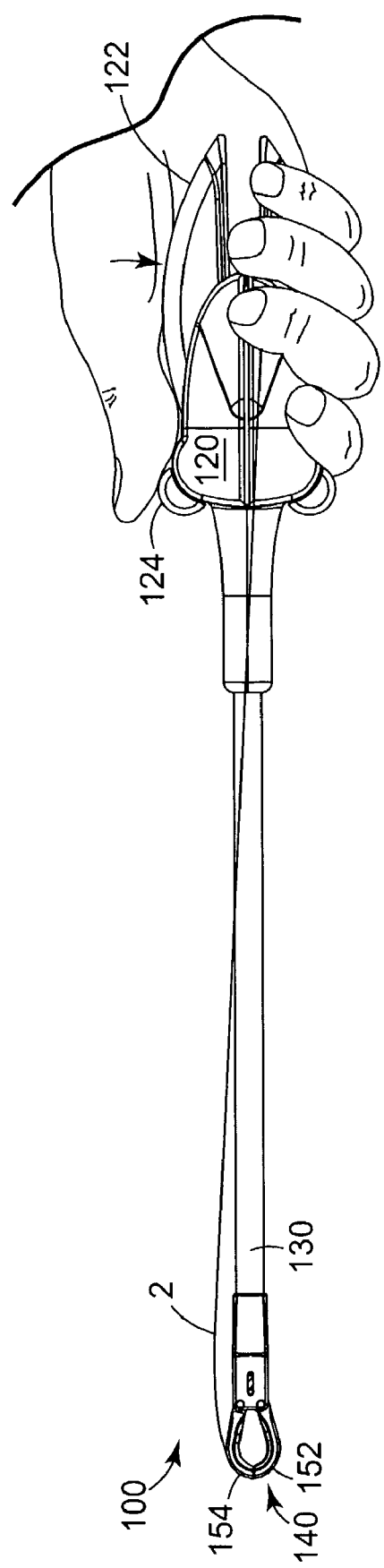
FIG. 20 is a side view of a device according to the present invention showing the jaws in a closed position.
Figure 21:
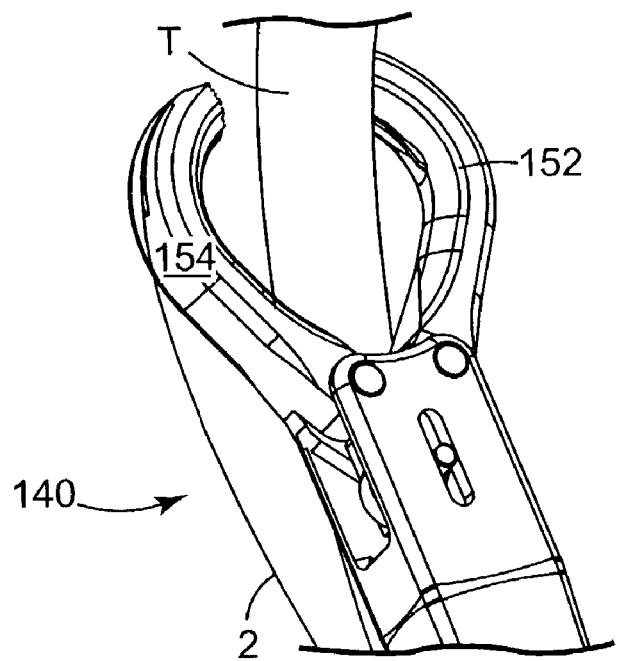
FIG. 21 is a perspective view of a distal portion of an instrument according to the present invention and tissue, showing the jaws slightly open.
Figure 22:
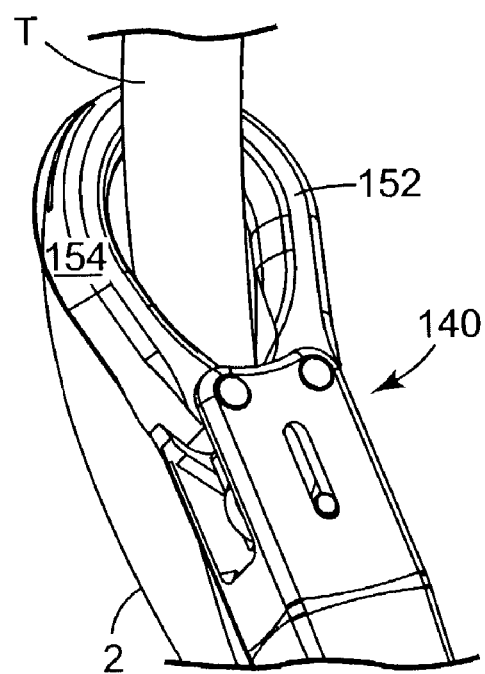
FIG. 22 is a perspective view of the device of FIG. 21 with the jaws in a closed position.

The device 100 is manually maneuvered around the tissue T to be sutured (FIG.'s 21 and 22). The surgeon then squeezes levers 122 together to close jaws around the selected tissue (FIG. 20). To inspect for tissue integrity, the surgeon may opt to keep the jaws closed and gently tug on the tissue T with the instrument 100. After the tissue has been selected, the surgeon may continue to grasp the tissue by keeping handles closed. The device 100 may optionally include a component (e.g. a releasable ratchet lock) for temporarily holding the jaws in this closed position.

Keeping the jaws closed, the surgeon may then pass the suture 2 through the tissue by retracting the firing member 124 toward the proximal end of the instrument 100, using either the thumb (FIG. 23) or index finger (not shown). The dart will pass into the dart capturing mechanism located in the dart receiving jaw 152. Pressure is preferably continuously applied to the levers 122, keeping the jaws closed while passing the dart.

To complete the suture passing process, the surgeon returns the suturing button 124 to its initial position by sliding the button 124 towards the distal end of the instrument with the thumb or index finger. This retracts the dart cam 142 into the jaw, and leaves the suture passed through the tissue.

The surgeon may then release the levers 122 allowing both the levers and the jaws to open. This will release the tissue that was sutured. The surgeon then withdraws the instrument 100 from the sutured site (FIG. 25).

To reload the instrument 100 and reuse it, one removes the dart from the receiving jaw 152 by grasping the suture and sliding the dart towards the levers 122 and into the keyhole slot (see FIG.'s 28-31). Once the dart reaches the keyhole slot, the dart 4 is removed by pulling on the suture 2, thereby releasing the dart from the keyhole slot 145A.

Once the dart 4 is removed from the device 100 and sufficient passes have been made, knots may be tied in the suture 2 to complete the suturing. If further suturing is required, some of the steps above can be repeated. Otherwise, the suture ends are cut to desired length and the dart 4 discarded appropriately.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical device for passing a suture and dart assembly, the device comprising.
    a body portion,
    an extension portion projecting distally from the body portion and comprising a longitudinal axis,
    a dart transport jaw and a dart capturing jaw, wherein both jaws are pivotable toward the longitudinal axis,
    a jaw manipulator capable of moving the jaws simultaneously toward the longitudinal axis and comprising a pair of moveable levers extending from the body portion,
    a firing member mounted on the body portion for movement relative to the body portion between prefired and fired positions;
    the dart transport jaw and the dart capturing jaw each having a major tissue gripping surface, the jaws being operatively associated with the jaw manipulator for movement between a release position with the major tissue gripping surfaces of the jaws spaced apart to receive tissue, and a clamped position with the major tissue gripping surfaces of the jaws spaced closer together than in the release position and adapted to manipulate tissue therebetween, the jaws being sized and shaped to define a tissue receiving region that is located proximal relative to the major tissue gripping surfaces when the jaws are in the clamped position,
    the dart transport jaw including a channel capable of being loaded with at least a portion of a suture and dart assembly,
    a firing assembly operatively associated with the firing member for passing the suture and dart assembly from the dart transport jaw to the dart capturing jaw when the jaws are in the clamped position, and
    the dart capturing jaw including a dart capturing member capable of associating the suture and dart assembly with the dart capturing jaw after the firing member is moved from the pre-fired to the fired position with the jaws in the clamped position,
    wherein the firing assembly includes a dart cam receivable within a substantially internal channel in the dart transport jaw, and wherein the suture and dart assembly comprises a dart,
    the dart cam having a distal surface adapted to engage a shoulder surface on the dart of the suture and dart assembly, and
    a pusher operatively associated with the firing member to move the dart cam from a retracted position situated within the channel of the dart transport jaw to a projecting position with at least a portion of the dart cam projecting beyond the major tissue gripping surface of the dart transport jaw when the firing member moves from the prefired to the fired position.

2. A device according to claim 1 wherein the dart cam includes a beveled distal end.

3. A device according to claim 1 wherein the dart cam has a centerline that follows a path as the pusher moves the dart cam from the retracted to the projecting position,
    the dart is substantially cone shaped with a tip and the shoulder surface,
    and the dart cam includes a beveled distal end that is shaped to abut the shoulder surface of the dart to drive the tip of the dart along a path that is substantially colinear with the path of distal point on the centerline of the dart cam during movement from the retracted to the projecting position.

4. A device according to claim 1 wherein the dart cam includes a slot for receiving a portion of a suture of the suture and dart assembly that is substantially adjacent a dart of the suture and dart assembly.

* * * * *

UNITED STATES PATENT AND TRADEMARK OFFICE
CERTIFICATE OF CORRECTION

| | | |
|---|---|---|
| PATENT NO. | : 7,615,059 B2 | Page 1 of 1 |
| APPLICATION NO. | : 10/155710 | |
| DATED | : November 10, 2009 | |
| INVENTOR(S) | : Watschke et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2118 days.

Signed and Sealed this

Nineteenth Day of October, 2010

David J. Kappos
*Director of the United States Patent and Trademark Office*